(12) United States Patent
Okada

(10) Patent No.: US 7,745,081 B2
(45) Date of Patent: Jun. 29, 2010

(54) DIPHENYL AMINE DERIVATIVE, PRODUCTION METHOD THEREFOR AND ELECTROPHOTOGRAPHIC PHOTOCONDUCTOR

(75) Inventor: Hideki Okada, Osaka (JP)

(73) Assignee: Kyocera Mita Corporation, Osaka (JP)

( * ) Notice: Subject to any disclaimer, the term of this patent is extended or adjusted under 35 U.S.C. 154(b) by 376 days.

(21) Appl. No.: 11/796,018

(22) Filed: Apr. 26, 2007

(65) Prior Publication Data

US 2007/0275314 A1 Nov. 29, 2007

(30) Foreign Application Priority Data

May 25, 2006 (JP) ............... 2006-145256
Nov. 27, 2006 (JP) ............... 2006-318879

(51) Int. Cl.
*G03G 5/047* (2006.01)
(52) U.S. Cl. ............... 430/58.75; 430/73; 564/434
(58) Field of Classification Search ............ 430/58.65, 430/72, 73, 58.75
See application file for complete search history.

(56) References Cited

U.S. PATENT DOCUMENTS 5,550,293 A * 8/1996 Shimada et al. ............ 564/426
5,654,481 A   8/1997 Anzai et al.

FOREIGN PATENT DOCUMENTS

| EP | 0 709 364 A1 * | 5/1996 |
| JP | 09-328456 | 12/1997 |
| JP | 9-328456 A * | 12/1997 |
| JP | 2005-206507 A * | 8/2005 |
| JP | 2005-289877 A | 10/2005 |

* cited by examiner

Primary Examiner—John L Goodrow
(74) Attorney, Agent, or Firm—Carmody & Torrance LLP

(57) ABSTRACT

The present invention provides a diphenyl amine derivative having the excellent solubility to a solvent and compatibility to a binding resin, an efficient production method therefor, and an electrophotographic photoconductor having the excellent sensitivity, capable of effectively preventing generation of the black dots. A diphenyl amine derivative represented by the following general formula (1) is used:

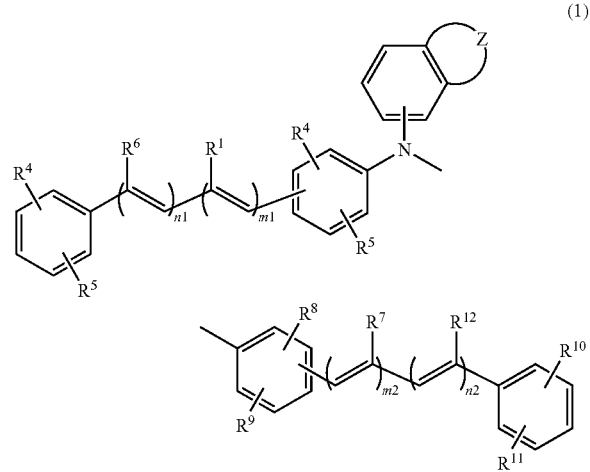

(1)

(In the general formula (1), $R^1$ to $R^{12}$ each are a hydrogen atom, an alkyl group which may have a substituent, or the like, Z is a ring structure linked with a benzene ring, which is a 4 to 8-membered ring including a hydrogen atom, a nitrogen atom, an oxygen atom, a carbon atom or a sulfur atom, m1, m2, n1, n2 each are 0 or 1, m1+n1 is 1 or 2, and m2+n2 is 1 or 2.)

9 Claims, 6 Drawing Sheets

DIPHENYL AMINE DERIVATIVE, PRODUCTION METHOD THEREFOR AND ELECTROPHOTOGRAPHIC PHOTOCONDUCTOR

BACKGROUND OF THE INVENTION

1. Field of the Invention

The present invention relates to a diphenyl amine derivative, a production method therefor and an electrophotographic photoconductor.

2. Description of the Related Art

An electrophotographic photoconductor having a conductive base member and a photoconductive layer provided on the conductive base member is known as the electrophotographic photoconductor used for an image forming apparatus, or the like. The electrophotographic photoconductor is produced by forming a photoconductive layer by applying an application liquid prepared by dissolving a hole transfer agent, a charge generating agent, a binding resin, and furthermore as needed, an electron transfer agent in a solvent onto a conductive base member and drying.

Moreover, as the hole transfer agent to be used, a triarylamine derivative is known. As the triarylamine derivative, for example, compounds represented by the following formulae (6-1) and (6-2) are known (Japanese Patent Application Laid-Open (JP-A) No. 2005-289877).

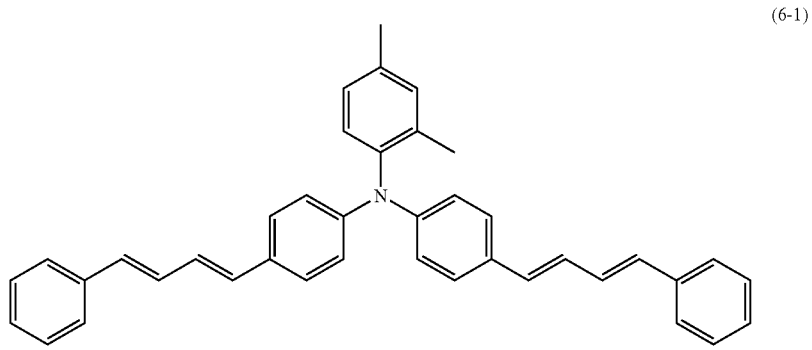

(6-1)

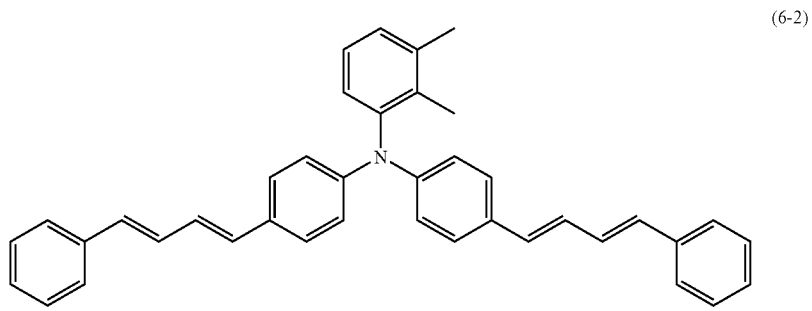

(6-2)

However, since the compounds represented by the formulae (6-1) and (6-2) have poor solubility to a solvent and poor compatibility to a binding resin, the sensitivity of the electrophotographic photoconductor has been insufficient. Furthermore, due to the poor solubility to a solvent and poor compatibility to a binding resin of the compounds represented by the formulae (6-1) and (6-2), they can easily be crystallized in a photoconductor layer so as to easily generate a problem of black dots in a synthesized image.

SUMMARY OF THE INVENTION

Accordingly, an object of the present invention is to provide a diphenyl amine derivative having the excellent solubility to a solvent and compatibility to a binding resin, capable of obtaining an electrophotographic photoconductor having the excellent sensitivity, an efficient production method therefor, and an electrophotographic photoconductor having the excellent sensitivity, capable of effectively preventing generation of the black dots.

A diphenyl amine derivative of the present invention is a compound represented by the following general formula (1):

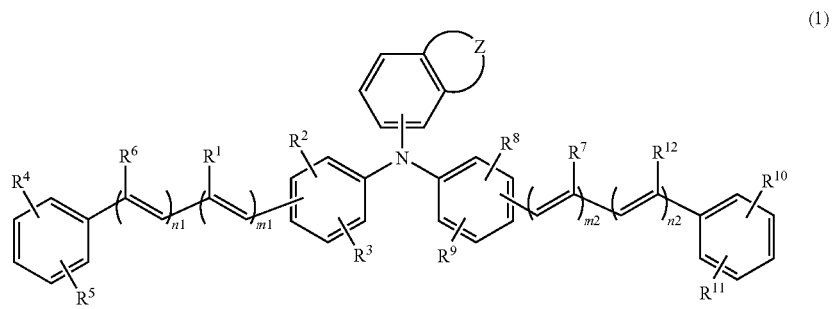

(1)

(In the general formula (1), $R^1$ to $R^{12}$ each are a hydrogen atom, an alkyl group which may have a substituent, an alkoxy group which may have a substituent, a phenoxy group which may have a substituent, an aryl group which may have a substituent, or an aralkyl group which may have a substituent, Z is a ring structure linked with a benzene ring, which is a 4 to 8-membered ring including a hydrogen atom, a nitrogen atom, an oxygen atom, a carbon atom or a sulfur atom, m1, m2, n1, n2 each are 0 or 1, m1+n1 is 1 or 2, and m2+n2 is 1 or 2.)

That is, according to the diphenyl amine derivative of the present invention, the excellent solubility to a solvent and the excellent compatibility to a binding resin can be realized. Therefore, according to the diphenyl amine derivative of the present invention, an electrophotographic photoconductor having the excellent sensitivity, capable of effectively restraining generation of the black dots can be obtained.

Moreover, at the time of providing the diphenyl amine derivative of the present invention, it is preferable that the ring structure including a benzene ring in the diphenyl amine derivative represented by the general formula (1) is a structure represented by the following formula (2-1) or (2-2):

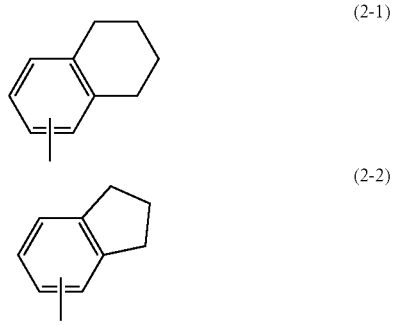

(2-1)

(2-2)

According to the configuration, a diphenyl amine derivative having further better solubility to a solvent and compatibility to a binding resin can be provided. Moreover, an electrophotographic photoconductor having a further better sensitivity, capable of effectively restraining generation of the black dots can be obtained.

Moreover, at the time of providing the diphenyl amine derivative of the present invention, it is preferable that when the ring structure including a benzene ring is represented by the formula (2-1), a nitrogen atom in the diphenyl amine derivative represented by the general formula (1) is bonded with the $5^{th}$ or $6^{th}$ place of the ring structure including a benzene ring, and when the ring structure including a benzene ring is represented by the formula (2-2), a nitrogen atom in the diphenyl amine derivative represented by the general formula (1) is bonded with the $4^{th}$ or $5^{th}$ place of the ring structure including a benzene ring.

According to the configuration, a diphenyl amine derivative having still better solubility to a solvent and compatibility to a binding resin can be provided. Moreover, an electrophotographic photoconductor having a still better sensitivity, capable of effectively restraining generation of the black dots can be obtained.

Moreover, at the time of providing the diphenyl amine derivative of the present invention, it is preferable that $R^1$ to $R^3$, $R^6$, $R^7$ to $R^9$ and $R^{12}$ in the general formula (1) area hydrogen atom.

According to the configuration, the charge transfer efficiency in the molecule of the diphenyl amine derivative can be further improved.

Moreover, another aspect of the present invention is a production method for the above-mentioned diphenyl amine derivative, including the following steps (A) to (B):

(A) a step of obtaining a compound represented by the following general formula (5) by reacting a compound represented by the following general formula (3) with a compound represented by the general formula (4a); and (B) a step of obtaining a diphenyl amine derivative represented by the general formula (1) by reacting the obtained compound represented by the general formula (5) with a compound represented by the following general formula (4b):

(3)

(In the general formula (3), Z is a ring structure linked to a benzene ring, which is a 4 to 8-membered ring including a hydrogen atom, a nitrogen atom, an oxygen atom, a carbon atom or a sulfur atom);

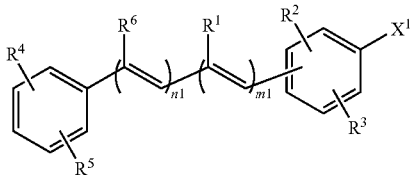

(4a)

(In the general formula (4a), $R^1$ to $R^6$ each are a hydrogen atom, an alkyl group which may have a substituent, an alkoxy group which may have a substituent, a phenoxy group which may have a substituent, an aryl group which may have a substituent, or an aralkyl group which may have a substituent, $X^1$ is a halogen atom, m1, n1 are each 0 or 1, and m1+n1 is 1 or 2);

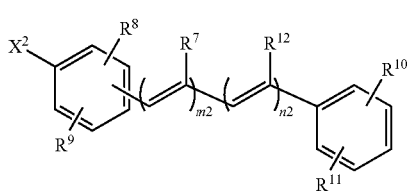

(4b)

(In the general formula (4b), $R^7$ to $R^{12}$ each are a hydrogen atom, an alkyl group which may have a substituent, an alkoxy group which may have a substituent, a phenoxy group which may have a substituent, an aryl group which may have a substituent, or an aralkyl group which may have a substituent, $X^2$ is a halogen atom, m2, n2 are each 0 or 1, and m2+n2 is 1 or 2); and

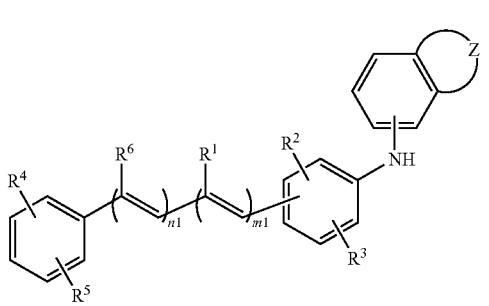

(5)

(In the general formula (5), $R^1$ to $R^6$ each are a hydrogen atom, an alkyl group which may have a substituent, an alkoxy group which may have a substituent, a phenoxy group which may have a substituent, an aryl group which may have a substituent, or an aralkyl group which may have a substituent, Z is a ring structure linked to a benzene ring, which is a 4 to 8-membered ring including a hydrogen atom, a nitrogen atom, an oxygen atom, a carbon atom or a sulfur atom, m1, n1 are each 0 or 1, and m1+n1 is 1 or 2.)

That is, since the production method including steps (A) to (B) is carried out, the diphenyl amine derivative represented by the general formula (1) can be produced efficiently.

Moreover, at the time of carrying out the production method for a diphenyl amine derivative of the present invention, it is preferable to use a palladium compound as a catalyst in steps (A) and (B), or in either of the steps.

According to the configuration, the yield rate of the diphenyl amine derivative in steps (A) to (B) can be further improved.

Moreover, at the time of carrying out the production method for a diphenyl amine derivative of the present invention, it is preferable to carry out steps (A) and (B), or either of the steps in the presence of a base.

According to the configuration, the catalyst activity of the above-mentioned palladium compound, or the like can be improved so as to further improve the yield rate of the diphenyl amine derivative according to steps (A) to (B) can be further improved.

Moreover, another aspect of the present invention is an electrophotographic photoconductor including a photoconductor layer provided on a conductive base member, wherein the photoconductor layer contains the above-mentioned diphenyl amine derivative.

That is, according to the electrophotographic photoconductor, the excellent sensitivity can be obtained as well as generation of the black dots can effectively be restrained.

Moreover, at the time of providing the electrophotographic photoconductor of the present invention, it is preferable that the photo conductor layer is a monolayer type photoconductor layer and the content of the diphenyl amine derivative is a value in a range of 20 to 500 parts by weight with respect to 100 parts by weight of the binding resin of the photoconductor layer.

According to the configuration, the production can be facilitated as well as the coating film defect can effectively be restrained.

Moreover, an electrophotographic photoconductor having the still better sensitivity can be obtained by further improving the dispersibility in the photoconductor layer of the diphenyl amine derivative.

Moreover, at the time of providing the electrophotographic photoconductor of the present invention, it is preferable that the photoconductor layer is a multilayer type photoconductor layer and the content of the diphenyl amine derivative is a value in a range of 10 to 500 parts by weight with respect to 100 parts by weight of the binding resin of the charge transfer layer included in the photoconductor layer.

According to the configuration, since the selection range of the charge generating agent and the photosensitive material other than a specific diphenyl amine derivative such as a charge transfer agent can be widened, the structure design can be fully improved.

Moreover, the electrophotographic photoconductor having a still better sensitivity can be obtained by further improving the dispersibility of the diphenyl amine derivative in the charge transfer layer.

BEST MODE FOR CARRYING OUT THE INVENTION

Diphenyl Amine Derivative

Figure 1:
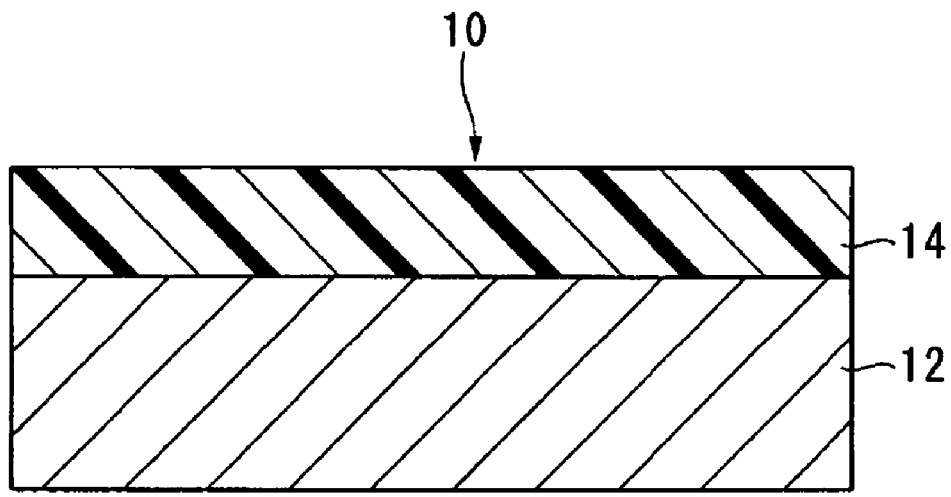
FIG. 1 is a schematic cross-sectional view showing an example of a monolayer type photoconductor.

A diphenyl amine derivative of the present invention is a compound represented by the following general formula (1). Hereafter, a compound represented by the general formula (1) will be referred to as a compound (1). Another compound is shown in the same manner.

(1)

(In the general formula (1), $R^1$ to $R^{12}$ each are a hydrogen atom, an alkyl group which may have a substituent, an alkoxy group which may have a substituent, a phenoxy group which may have a substituent, an aryl group which may have a substituent, or an aralkyl group which may have a substituent, Z is a ring structure linked with a benzene ring, which is a 4 to 8-membered ring including a hydrogen atom, a nitrogen atom, an oxygen atom, a carbon atom or a sulfur atom, m1, m2, n1, n2 each are 0 or 1, m1+n1 is 1 or 2, and m2+n2 is 1 or 2.)

Examples of the above-mentioned alkyl group include a methyl group, an ethyl group, a propyl group, an isopropyl group, a n-butyl group, a t-butyl group, a pentyl group, an isopentyl group, a neopentyl group, and a hexyl group.

Moreover, examples of the alkoxy group include a methoxy group, an ethoxy group, a n-propoxy group, an isopropoxy group, a n-butoxy group, a s-butoxy group, a t-butoxy group, a pentyloxy group, an isopentyloxy group, a neopentyloxy group, and a hexyloxy group.

Moreover, examples of the aryl group include a phenyl group, a tolyl group, a xylyl group, a mesityl group, a naphtyl group, an anthryl group, and a phenanthryl group.

Moreover, examples of the aralkyl group include a benzyl group, an α-methyl benzyl group, a phenethyl group, a styryl group, a cinnamyl group, a 3-phenyl propyl group, a 4-phenyl butyl group, a 5-phenyl pentyl group, and a 6-phenyl hexyl group.

Moreover, as $R^1$ to $R^{12}$, a hydrogen atom, an alkyl group and an aryl group are preferable, and a hydrogen atom is further preferable.

It is more preferable that $R^1$ to $R^3$, $R^6$, $R^7$ to $R^9$ and $R^{12}$ are a hydrogen atom.

The reason thereof is that the charge transfer efficiency in the molecule of a specific diphenyl amine derivative can be further improved by providing $R^1$ to $R^3$, $R^6$, $R^7$ to $R^9$ and $R^{12}$ as a hydrogen atom.

That is, since these substituents are a hydrogen atom, spread of a π electron as the transfer path of the charge can be in a preferable state.

Moreover, m1, m2, n1, n2 are each 0 or 1, m1+n1 is 1 or 2, and m2+n2 is 1 or 2.

Moreover, it is particularly preferable that the ring structure including a benzene ring in a diphenyl amine derivative represented by the general formula (1) is a structure represented by the formula (2-1) or (2-2).

(2-1)

-continued (2-2)

The reason thereof is that a diphenyl amine derivative having still better solubility to a solvent and compatibility to a binding resin can be provided by including the ring structure represented by the formula (2-1) or (2-2). Moreover, an electrophotographic photoconductor having a still better sensitivity, capable of effectively restraining generation of the black dots can be obtained.

That is, since the ring structure Z linked to a benzene ring is cyclohexyl or cyclopentyl, the various characteristics such as the asymmetric property and the plane property of a specific diphenyl amine derivative can be adjusted in a further preferable range.

Moreover, examples of another ring structure including a benzene ring include, as represented by the following formulae (2-3) to (2-7), those having a ring structure linked to a benzene ring as cyclobutyl, cycloheptyl, cyclooctyl, a saturated dioxy ring, or the like.

(2-3)

(2-4)

(2-5)

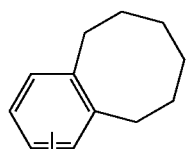

(2-6)

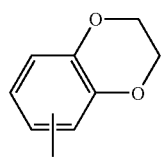

(2-7)

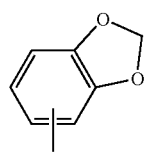

Moreover, it is preferable that when the ring structure including a benzene ring is represented by the formula (2-1), a nitrogen atom in the diphenyl amine derivative represented by the general formula (1) is bonded with the $5^{th}$ or $6^{th}$ place of the ring structure including a benzene ring, and when the ring structure including a benzene ring is represented by the formula (2-2), a nitrogen atom in the diphenyl amine derivative represented by the general formula (1) is bonded with the $4^{th}$ or $5^{th}$ place of the ring structure including a benzene ring.

The reason thereof is that a diphenyl amine derivative having still better solubility to a solvent and compatibility to a binding resin can be provided by accordingly specifying the position of the ring structure Z linked to the benzene ring. Moreover, an electrophotographic photoconductor having a further better sensitivity, capable of effectively restraining generation of the black dots can be obtained.

That is, by specifying the position of the ring structure Z linked to the benzene ring to a predetermined position, the various characteristics such as the asymmetric property and the plane property of a specific diphenyl amine derivative can be adjusted in a still preferable range.

Moreover, examples of the compound (1) include compounds (1-1) to (1-12).

(1-1)

(1-2)

(1-3)

(1-4)

(1-5)

(1-6)

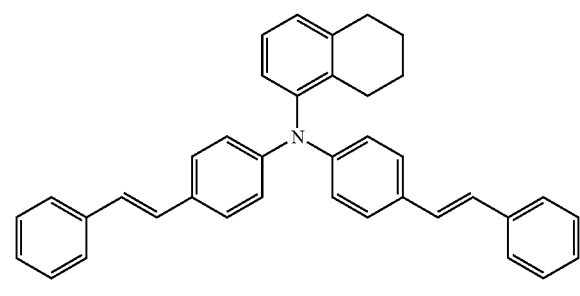

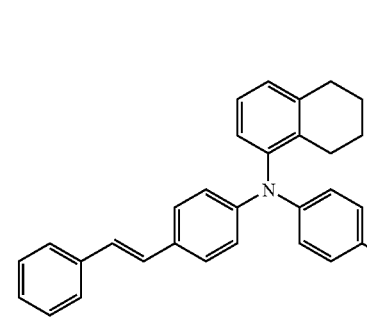

-continued (1-7)
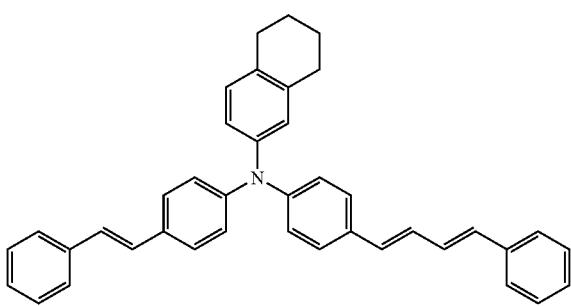

(1-8)
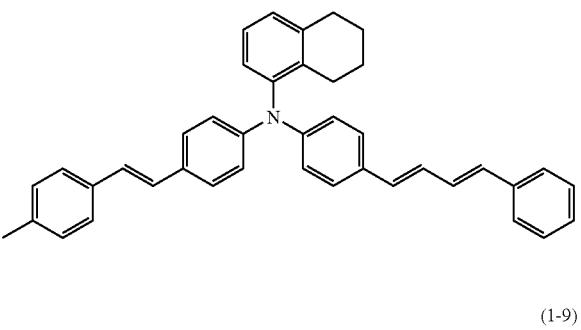

(1-9)

(1-10)
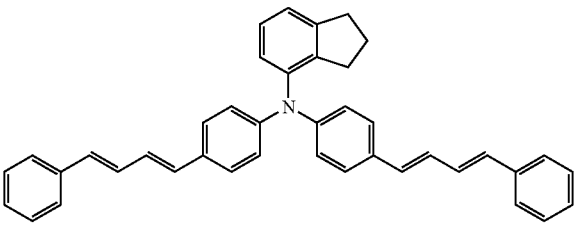

(1-11)
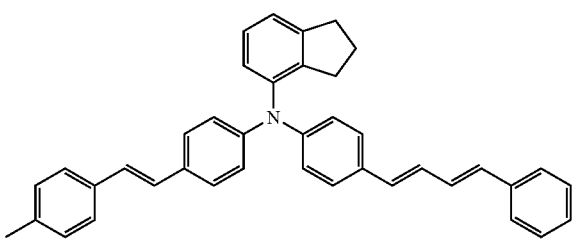

(1-12)
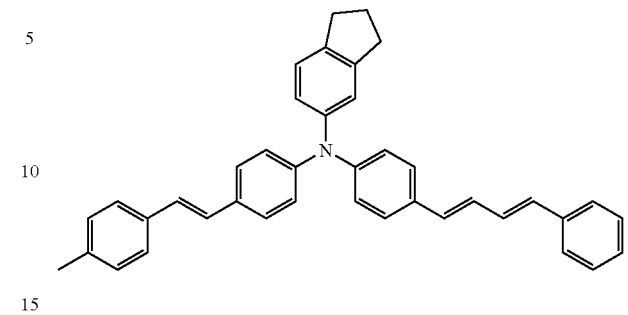

<Production Method for a Diphenyl Amine Derivative>

A compound (1) is produced for example as follows. In the reaction formula, $X^1$ to $X^4$ are each a halogen atom, and $R^1$ to $R^{12}$, m1, m2, n1 and n2 are same as the description for the formula (1).

(Preparation Step)

The step is a step for obtaining compounds (4a) and (4b). It is preferable that this step includes the following steps (a) to (b).

Since the compounds (4a) and (4b) can be obtained in the same manner, the step of obtaining the compound (4a) will be mainly explained.

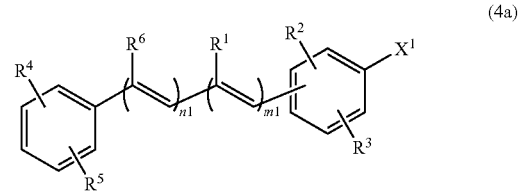
(4a)

(In the general formula (4a), $R^1$ to $R^6$ are each a hydrogen atom, an alkyl group which may have a substituent, an alkoxy group which may have a substituent, a phenoxy group which may have a substituent, an aryl group which may have a substituent, or an aralkyl group which may have a substituent, $X^1$ is a halogen atom, m1, n1 are each 0 or 1, and m1+n1 is 1 or 2.)

For example, in the case where n1=1, m1=0 or 1, a compound (4a') can be obtained by step (a-1) and step (b-1), and in the case where m1=1, n1=0 or 1, a compound (4a'') can be obtained by step (a-2) and step (b-2).

Step (a-1)

First, a compound (7) and a triethyl phosphite are reacted for obtaining a compound (8), and then an unreacted triethyl phosphite is removed under reduced pressure.

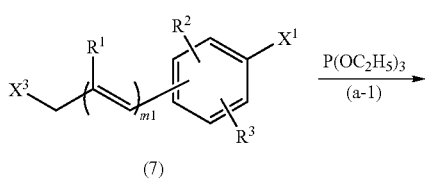
(7)

-continued

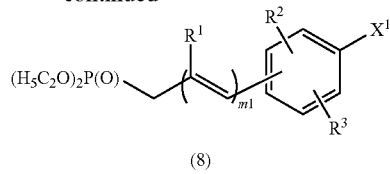

(8)

At the time, the reaction ratio (mole ratio) of the compound (7) and the triethyl phosphite is preferably 1:1 to 1:2.5. If the triethyl phosphite is too little, the yield rate of the compound (8) becomes poor. If the triethyl phosphite is too much, the unreacted triethyl phosphite is increased so that refinement of the compound (8) may be difficult.

Moreover, the reaction temperature is preferably 160 to 200° C., and the reaction time is preferably 2 to 10 hours. According to the range, desired reaction may be carried out efficiently with relatively simple production equipment.

Step (b-1)

Then, in the presence of a catalyst, the compound (8) and a compound (9) are reacted in a solvent for obtaining a compound (4a') (Wittig reaction), and the compound (4a') is extracted and refined.

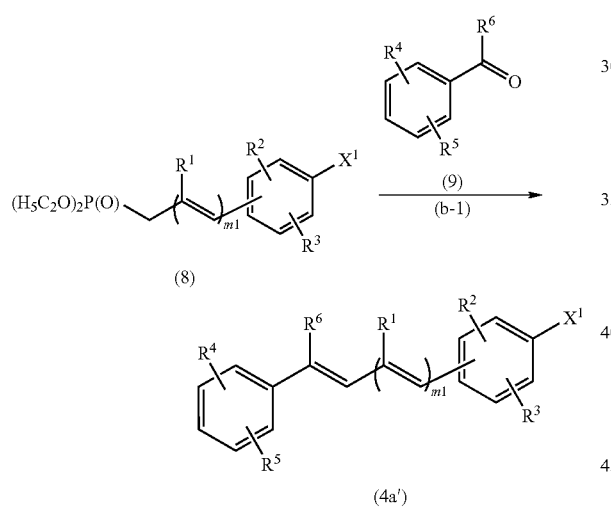

At the time, the reaction ratio (mole ratio) of the compound (8) and the compound (9) is preferably 1:1 to 1:2.5. If the compound (8) is too little, the yield rate of the compound (4a') becomes poor. If the compound (8) is too much, the unreacted compound (8) is increased so that refinement of the compound (4a') may be difficult.

Moreover, the reaction temperature is preferably −20 to 30° C., and the reaction time is preferably 5 to 30 hours. According to the range, desired reaction can be carried out efficiently with relatively simple production equipment.

Moreover, examples of the catalyst include sodium alkoxides such as sodium methoxide, and sodium ethoxide; metal hydrogenated products such as hydrogenated sodium and hydrogenated potassium; and metal salts such as n-butyl lithium. The catalysts may be used alone by one kind or as a combination of two or more kinds.

Moreover, the addition quantity of the catalyst is preferably 1 to 2 moles with respect to 1 mole of the compound (9). If the addition quantity of the catalyst is below 1 mole, the reactivity of the compound (8) and the compound (9) may be remarkably lowered. If the addition quantity of the catalyst is above 2 moles, the reaction of the compound (8) and the compound (9) may hardly be controlled.

Moreover, examples of the solvent include ethers such as a diethyl ether, a tetrahydrofuran and a dioxane; halogenated hydrocarbons such as methylene chloride, a chloroform and a dichloroethane; and aromatic hydrocarbons such as a benzene and a toluene.

Step (a-2)

First, in the same manner as in the above-mentioned step (a-1), a compound (10) and a triethyl phosphite are reacted for obtaining a compound (11), and then an unreacted triethyl phosphite is removed under reduced pressure.

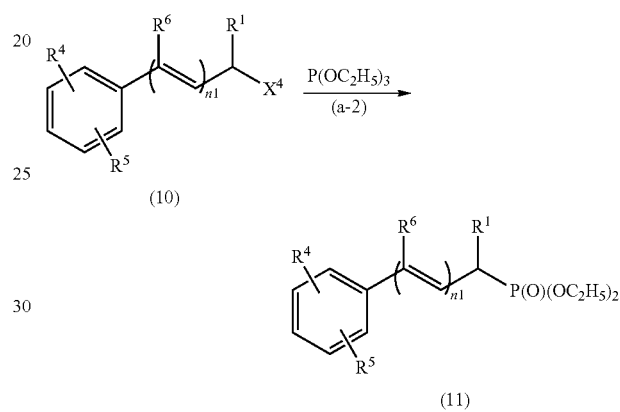

Step (b-2)

Then, in the same manner as in the above-mentioned step (b-1), the compound (11) and a compound (12) are reacted in a solvent in the presence of a catalyst for obtaining a compound (4a") (Wittig reaction), and the compound (4a") is extracted and refined.

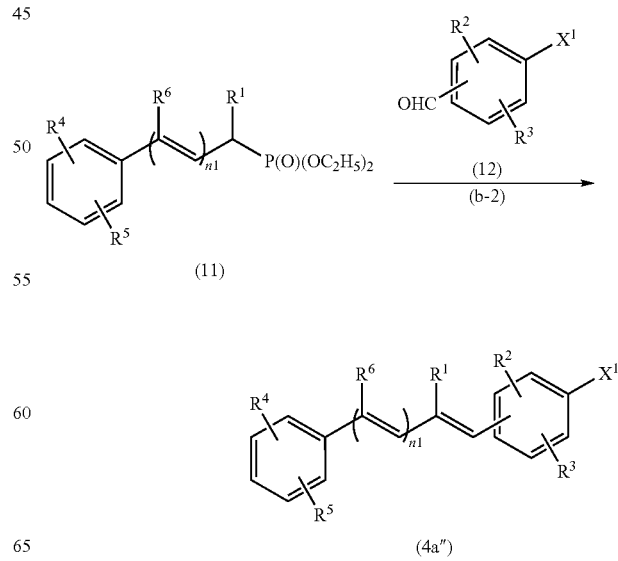

As mentioned above, a compound (4b) can be obtained in the same manner as in steps (a) to (b).

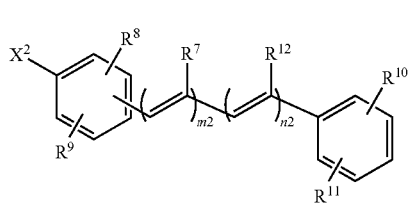

(4b)

(In the general formula (4b), $R^7$ to $R^{12}$ are each a hydrogen atom, an alkyl group which may have a substituent, an alkoxy group which may have a substituent, a phenoxy group which may have a substituent, an aryl group which may have a substituent, or an aralkyl group which may have a substituent, $X^2$ is a halogen atom, m2, n2 are each 0 or 1, and m2+n2 is 1 or 2.)

Step (A)

Subsequently, in the presence of a catalyst, or the like, a compound (4a) and a compound (3) are reacted in a solvent for obtaining a compound (5) (coupling reaction), and the compound (5) is extracted and refined. In the case the compound (4a) and the compound (4b) are the same compound, a compound (1) as the final target produce will be obtained in step (A) with the amount of the compound (4a) in step (A) doubled and step (B) to be described later omitted.

Z in the compound (3) is a ring structure linked to a benzene ring, which is a 4 to 8-membered ring including a hydrogen atom, a nitrogen atom, an oxygen atom, a carbon atom or a sulfur atom.

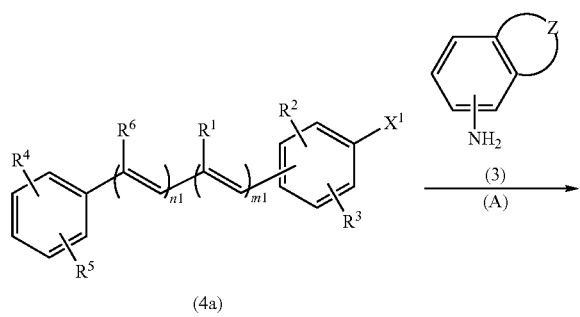

(4a)

(3)

(A)

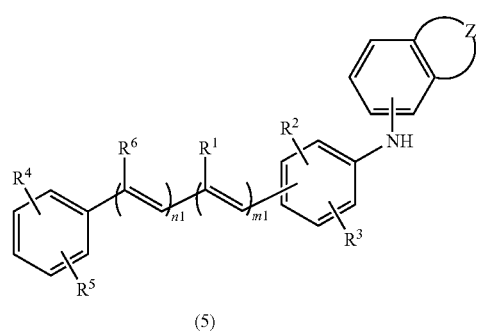

(5)

At the time, the reaction ratio (mole ratio) of the compound (4a) and the compound (3) is preferably 1:1 to 1:2. If the compound (4a) is too little, the yield rate of the compound (5) becomes poor. If the compound (4a) is too much, the unreacted compound (4a) is increased so that refinement of the compound (5) may be difficult.

Moreover, the reaction temperature is preferably 80 to 140° C., and the reaction time is preferably 2 to 10 hours. According to the range, desired reaction can be carried out efficiently with relatively simple production equipment.

Moreover, it is preferable to use a palladium compound as the catalyst.

The reason thereof is that the yield rate of a specific diphenyl amine derivative can be further improved in step (A) by the use of palladium compound as the catalyst.

That is, with the palladium compound, the activating energy of the reaction in step (A) can effectively lowered.

Examples of such a palladium compound include tetravalent palladium compounds such as a sodium hexachloropalladium (IV) tetrahydrate and a potassium hexachloropalladium (IV) tetrahydrate; divalent palladium compounds such as palladium chloride (II), palladium bromide (II), palladium acetate (II), palladium acetyl acetate (II), dichlorobis (benzonitrile) palladium (II), dichlorobis (triphenyl phosphine) palladium (II), dichlorotetramine palladium (II) and dichloro (cycloocta-1,5-diene) palladium (II); and palladium compounds such as tris (dibenzylidene acetone)dipalladium (O), tris (dibenzylidene acetone) dipalladium chloroform complex (O) and tetrakis (triphenyl phosphine) palladium (O).

Moreover, the catalysts may be used either alone by one kind or in a combination of two or more kinds.

It is preferable to have the addition quantity of the palladium compound as a value in a range of 0.00025 to 10 moles with respect to 1 mole of the compound (3).

Moreover, it is preferable to carry out step (A) in the presence of a base.

The reason thereof is that by carrying out step (A) in the presence of a base, the halogenated hydrogen generated in the vessel can rapidly be neutralized so as to consequently improve the catalyst activity so that the yield rate of a specific diphenyl amine derivative in step (A) can be further improved.

Moreover, the base can be selected from inorganic bases and organic bases without specific limitation. Alkaline metal alkoxides such as sodium methoxide, sodium ethoxide, potassium methoxide, potassium ethoxide, lithium-tert-butoxide, sodium-tert-butoxide and potassium-tert-butoxide are preferable, and sodium-tert-butoxide is particularly preferable. Moreover, inorganic bases such as tripotassium phosphate and cesium fluoride are also effective.

Moreover, as to the addition quantity of the base, although it also depends on the amount of the palladium compound, it is preferably a value in a range of 0.995 to 5 moles for example in the case where 0.005 mole of the palladium compound is added to 1 mole of the N—H bond of the compound (3).

Examples of the solvent include xylene.

Step (B)

Then, in the presence of a catalyst, a compound (5) and a compound (4b) are reacted in a solvent for obtaining a compound (1) (coupling reaction), and the compound (1) is extracted and refined.

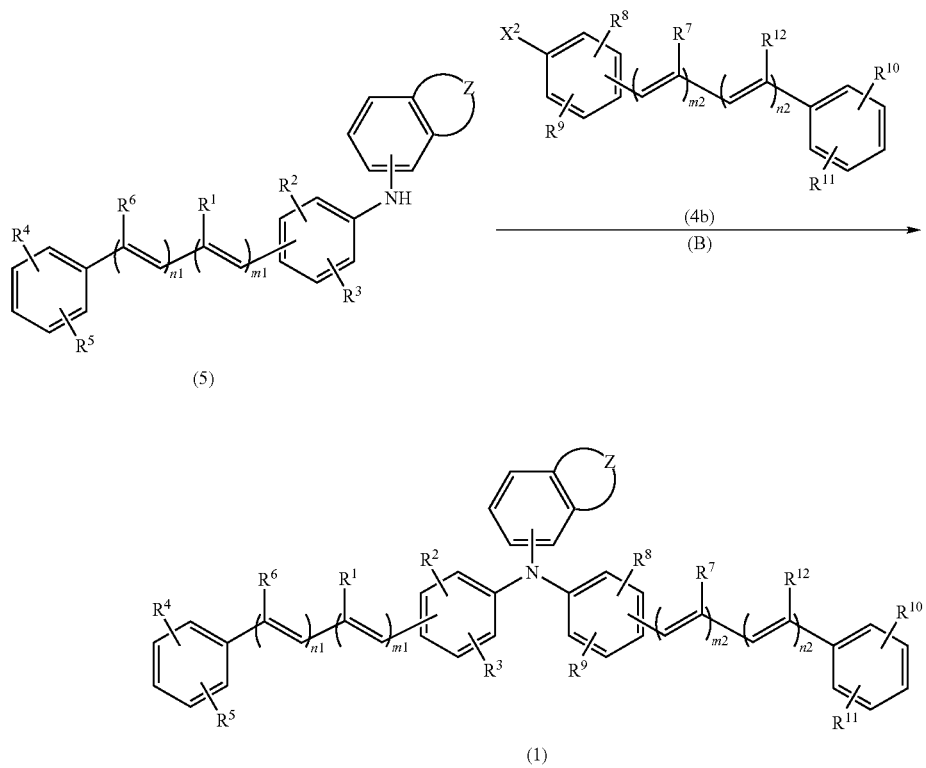

At the time, the reaction ratio of the compound (5) and the compound (4b) is preferably 1:1 to 1:2. If the compound (5) is too little, the yield rate of the compound (1) becomes poor. If the compound (5) is too much, the unreacted compound (5) is increased so that refinement of the compound (1) may be difficult.

Moreover, the reaction temperature is preferably 80 to 140° C., and the reaction time is preferably 2 to 10 hours. According to the range, desired reaction can be carried out efficiently with relatively simple production equipment.

Examples of the catalyst, base, solvent, and the like include those same as step (A).

Since the compound (1) heretofore explained has a nitrogen atom bonded with a predetermined ring structure including a benzene ring, it has the solubility to a solvent and the compatibility to a binding resin superior to the compounds (6-1), (6-2).

<Electrophotographic Photoconductor>

The electrophotographic photoconductor of the present invention is an electrophotographic photoconductor including a photoconductor layer provided on a conductive base member, with the photoconductor layer containing a diphenyl amine derivative of the present invention (compound (1)).

Examples of the electrophotographic photoconductor include a (i) monolayer type photo conductor and a (ii) multilayer type photoconductor. For the advantages including applicability to the charge type photoconductors of the positive and negative types, the simple structure facilitating the production, capability of effectively restraining the coating film defect at the time of forming the photoconductor layer, little inter-layer interface so as to easily improve the optical characteristics, of the like, the (i) monolayer type photoconductor is preferable.

(i) Monolayer Type Photoconductor

FIG. 1 is a schematic cross-sectional view showing an example of a monolayer type photoconductor. The monolayer type photoconductor 10 has a conductive base member 12, and a photoconductor layer 14 provided on the conductive base member 12.

Figure 2:
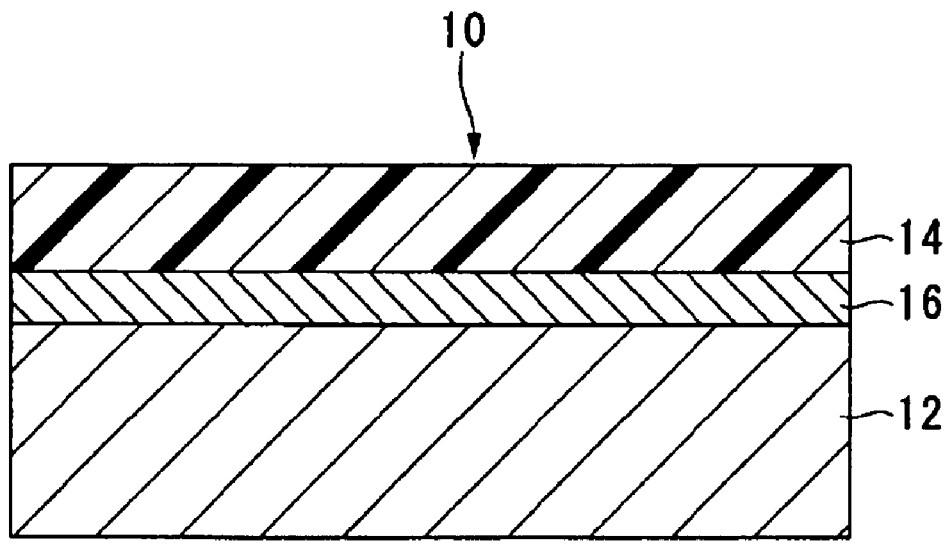
FIG. 2 is a schematic cross-sectional view showing another example of a monolayer type photoconductor.
Figure 3:
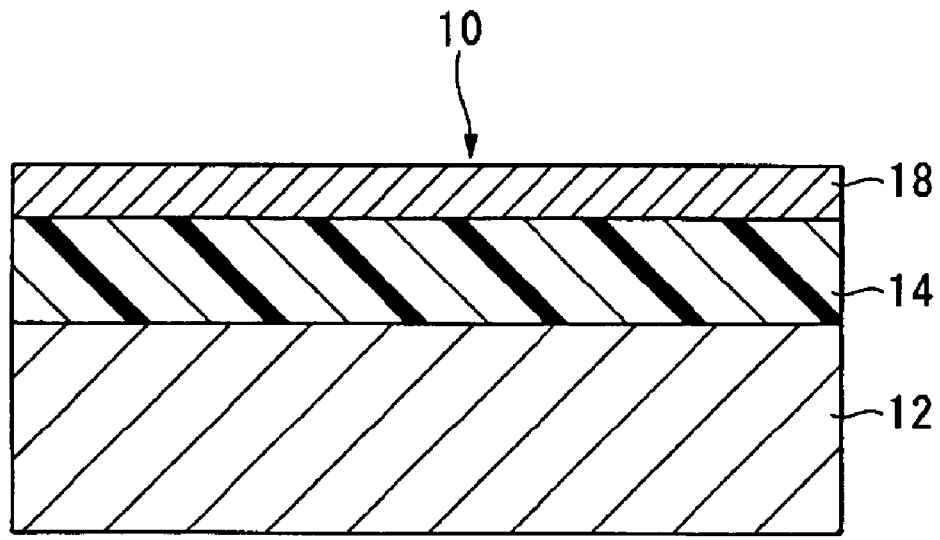
FIG. 3 is a schematic cross-sectional view showing another example of a monolayer type photoconductor.

The signal layer type photoconductor 10 is not limited to that of FIG. 1. As shown in FIG. 2, a barrier layer 16 may be provided between the conductive base member 12 and the photoconductor layer 14 in a range not to inhibit the characteristics of the monolayer type photoconductor 10, or as shown in FIG. 3, a protection layer 18 may be provided on the surface of the photoconductor layer 14.

Moreover, examples of the conductive base member include metals such as an iron, an aluminum, a copper, a tin, a platinum, a silver, a vanadium, a molybdenum, a chromium, a cadmium, a titanium, a nickel, a palladium, an indium, a stainless steel and a brass; plastic materials with the metals deposited or laminated; and glasses covered with an aluminum iodide, a tin oxide and an indium oxide.

Moreover, the shape of the conductive base member may be, for example, a sheet-like or a drum-like. The shape of the conductive base member may be determined optionally according to the structure of the image forming apparatus.

Moreover, the thickness of the photoconductor layer is preferably 5 to 100 μm, and more preferably 10 to 50 μm.

The photoconductor layer is a layer containing for example a hole transfer agent, a charge generating agent, a binding resin, and as needed an electron transfer agent.

Moreover, the photoconductor layer contains as the hole transfer agent a compound (1).

Moreover, the photoconductor layer may contain another hole transfer agent. Examples of another hole transfer agent include a nitrogen containing cyclic compound and condensation polycyclic compounds including triaryl amine based compounds excluding the compound (1); oxadiazol based compounds such as a 2,5-di(4-methyl amino phenyl)-1,3,4-oxadiazol; styryl based compounds such as 9-(4-diethyl amino styryl) anthracene; carbazol based compounds such as a polyvinyl carbazol; organic polysilane compounds; pyrazoline based compounds such as a 1-phenyl-3-(p-dimethyl amino phenyl) pyrazoline; hydrazone based compounds; indole based compounds; oxazole based compounds; isooxazole based compounds; thiazol based compounds; tiadiazol compounds; imidazol based compounds; pyrazole based compounds; and triazole based compounds. The hole transfer agents may be used either alone by one kind or in a combination of two or more kinds.

Moreover, examples of the charge generating agent include organic photoconductors such as a phthalocyanine based pigment, a perylene based pigment, a bisazo pigment, a diochetopyrolopyrol pigment, a non-metal naphthalocyanine pigment, a metal naphthalocyanine pigment, a squaline pigment, a trisazo pigment, an indigo pigment, an azulenium pigment, a cyanine pigment, a pyririum pigment, an anthenthrone pigment, a triphenyl methane based pigment, a thlene pigment, a toluizine based pigment, a pyrazoline based pigment and a quinacrydone based pigment; and inorganic photoconductors such as a selenium, a selenium-tellurium, a selenium-arsenic, a cadmium sulfide, and an amorphous silicone. The charge generating agents may be used either alone by one kind or in a combination of two or more kinds.

Moreover, the charge generating agent is preferably at least one selected from the group consisting of a non metal phthalocyanine (σ type or X type), a titanyl phthalocyanine (α type or Y type), a hydroxyl gallium phthalocyanine (V type) and a chlorogallium phthalocyanine (II type) since an electrophotographic photoconductor having further better sensitivity characteristics, electric characteristics, stability, or the like, can be obtained in the case of using the hole transfer agent and the electron transfer agent in combination.

Moreover, examples of the electron transfer agent include a quinone derivative, an anthraquinone derivative, a maronic anhydride, a thiopyrane derivative, a trinitrothioxantone derivative, a 3,4,5,7-tetranitro-9-fluorenone derivative, a dinitroanthracene derivative, a dinitroacrydine derivative, a nitroanthraquinone derivative, a dinitroanthraquinone derivative, tetracyanoethylene, 2,4,8-trinitrothioxantone, dinitrobenzene, dinitroanthracene, dinitroacrydine, nitroanthraquinone, dinitroanthraquinone, succinic anhydride, maleic anhydride, and dibromomaleic anhydride. The electron transfer agents may be used either alone by one kind or in a combination of two or more kinds.

Moreover, a quinone derivative is preferable as the electron transfer agent since it can provide an electrophotographic photoconductor having the excellent electron accepting property and compatibility to the charge generating agent, sensitivity characteristics and endurance. Examples of the quinone derivative include a naphthoquinone derivative, a diphenoquinone derivative, and an azoquinone derivative.

As the electron transfer agent, compounds (13-1) to (13-4) are particularly preferable.

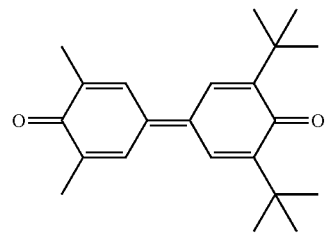

(13-1)

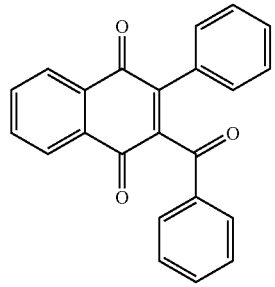

(13-2)

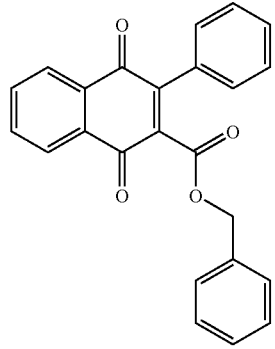

(13-3)

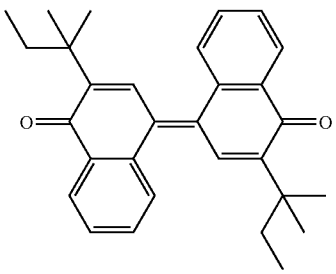

(13-4)

Examples of the binding resin include thermoplastic resins such as a polycarbonate resin of a bisphenol Z type, a bisphenol ZC type, a bisphenol C type, a bisphenol A type, or the like, a polyallylate resin, a styrene-butadiene copolymer, a styrene-acrylonitrile copolymer, a styrene-maleic acid copolymer, an acrylic copolymer, a styrene-acrylic acid copolymer, a polyethylene resin, an ethylene-vinyl acetate copolymer, a chlorinated polyethylene resin, a polyvinyl chloride resin, a polypropylene resin, an ionomer resin, a vinyl chloride-vinyl acetate copolymer, an alkyd resin, a polyamide resin, a polyurethane resin, a polysulfone resin, a diallyl phthalate resin, a ketone resin, a polyvinyl butylal resin, and a polyether resin; thermosetting resins such as a silicone resin, an epoxy resin, a phenol resin, a urea resin and a melamine resin; and photocuring resins such as an epoxy acrylate and a urethane-acrylate. The binding resin may be used alone by one kind or as a combination of two or more kinds.

Moreover, the photoconductor layer may contain a known additive in a range not to pose an adverse effect to the electrophotographic characteristics. Examples of the additive include a degradation inhibitor including an antioxidant, a radical supplement agent, a singlet quencher, and a ultraviolet absorbing agent, a tenderizer, a plasticizer, a surface reforming agent, an extending agent, a thickener, a dispersion stabilizer, a wax, an acceptor, and a donor.

Moreover, for improving the sensitivity of the photoconductor layer, a known sensitizer such as terphenyl, halonaphthquinone, and acenaphthylene may be used in combination with a charge generating agent.

Moreover, it is preferable that the content of the hole transfer agent including a specific diphenyl amine derivative is 20 to 500 parts by weight with respect to 100 parts by weight of the binding resin of the photoconductor layer.

The reason thereof is that by providing the content of the hole transfer agent including a specific diphenyl amine derivative in a value in such a range, an electrophotographic photoconductor having a still better sensitivity can be obtained by further improving the dispersibility in the photoconductor layer of the specific diphenyl amine derivative.

That is, if the content of the specific diphenyl amine derivative is of a value of below 20 parts by weight, the sensitivity is lowered so as to generate a trouble in the practical use. If the content of such a specific diphenyl amine derivative is of a value of above 500 parts by weight, on the other hand, crystallization of the specific diphenyl amine derivative is excessively facilitated so that the photoconductor layer may hardly be formed adequately.

Therefore, it is more preferable that the content of such a specific diphenyl amine derivative is of a value in a range of 30 to 200 parts by weight.

Moreover, the content of the charge generating agent is preferably 0.1 to 50 parts by weight with respect to 100 parts by weight of the binding resin, and more preferably 0.5 to 30 parts by weight.

In the case the electron transfer agent is contained, the content of the electron transfer agent is preferably 5 to 100 parts by weight with respect to 100 parts by weight of the binding resin, and more preferably 10 to 80 parts by weight.

Moreover, the photoconductor layer is formed by applying on a conductive base member a application liquid prepared by dissolving or dispersing a hole transfer agent, a charge generating agent, a binding resin, and as needed, an electron transfer agent in a solvent, and drying.

Moreover, the application liquid is prepared by dissolving or dispersing the components in a solvent, using a roll mill, a ball mill, an atliter, a paint shaker, a ultrasonic dispersing machine, or the like. As to the coating method, a known method may be used.

Examples of the solvent include alcohols such as methanol, ethanol, isopropanol, and butanol; aliphatic hydrocarbons such as n-hexane, octane, and cyclohexane; aromatic hydrocarbons such as benzene, toluene, xylene; halogenated hydrocarbons such as dichloromethane, dichlorothane, chloroform, carbon tetrachloride, and chlorobenzene; ethers such as dimethyl ether, diethyl ether, tetrahydrofuran, ethylene glycol dimethyl ether, and diethylene glycol dimethyl ether; ketones such as acetone, methyl ethyl ketone, and cyclohexanone; esters such as ethyl acetate, and methyl acetate; dimethyl formaldehyde; dimethyl formamide; and dimethyl sulfoxide. The solvents may be used alone by one kind or as a combination of two or more kinds.

For improving the dispersibility of the components and the smoothness of the photoconductor layer surface, a surfactant, a leveling agent, or the like may be added to the application liquid.

Moreover, since the monolayer type photoconductor contains the compound (1) in the photoconductor layer, the residual potential is lowered and the sensitivity is high. Furthermore, in the case where the photoconductor layer contains an electron transfer agent, transfer of the electrons is carried out efficiently between the charge generating agent and the hole transfer agent so that the sensitivity, or the like tends to be further stabilized.

(ii) Multilayer Type Photoconductor

Figure 4:
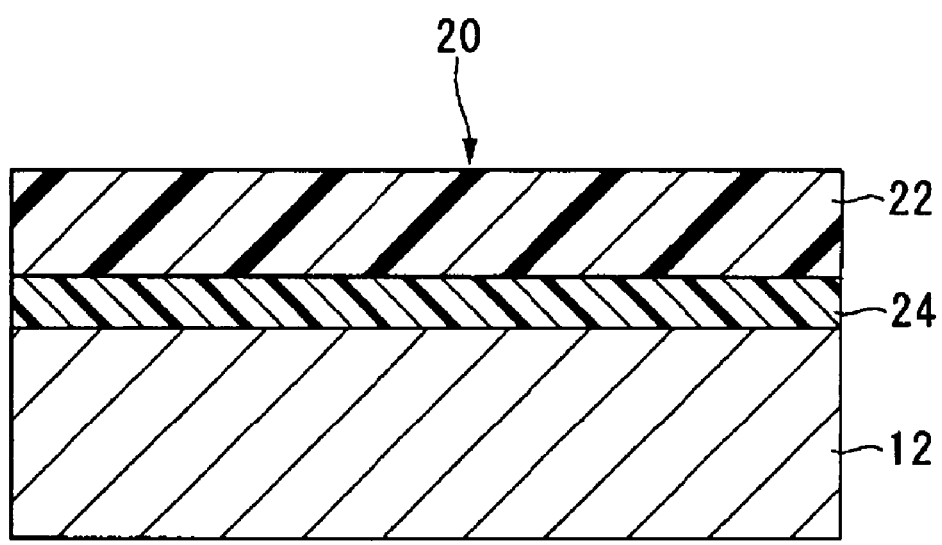
FIG. 4 is a schematic cross-sectional view showing an example of a multilayer type photoconductor.

FIG. 4 is a schematic cross-sectional view showing an example of a multilayer type photoconductor. The multilayer type photoconductor 20 has a conductive base member 12, a charge generating layer 24 containing a charge generating agent, provided on the conductive base member 12, and a charge transfer layer 22 provided on the charge generating layer 24. In the multilayer type photoconductor 20, the charge generating layer 24 and the charge transfer layer 22 provide a photoconductor layer.

In the case such a multilayer type photoconductor layer is adopted, it is advantageous in that the selection range of the photosensitive materials such as the charge generating agent and the charge transfer agent other than the specific diphenyl amine derivative can be widened so as to improve the freedom of the structure design.

Figure 5:
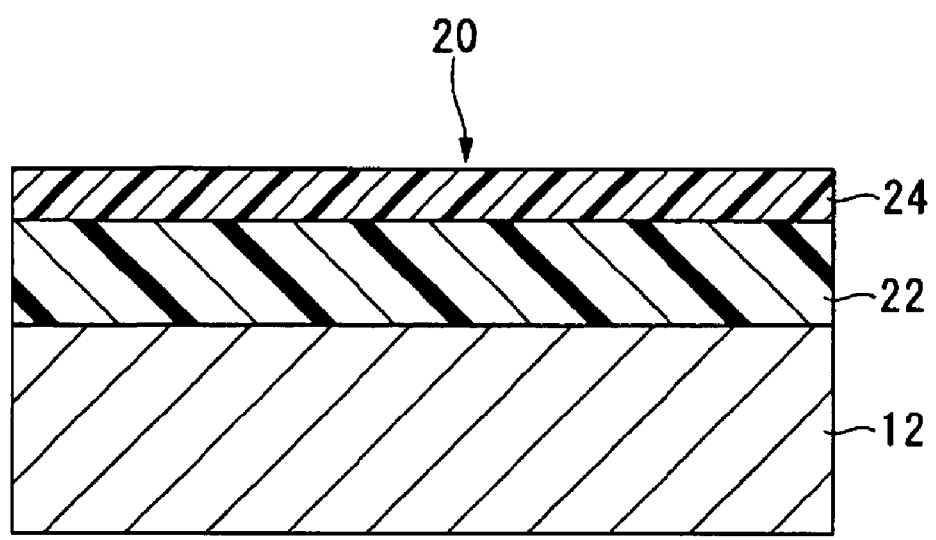
FIG. 5 is a schematic cross-sectional view showing another example of a multilayer type photoconductor.

The multilayer type photoconductor 20 is not limited to that of FIG. 4, and the charge transfer layer 22 may be provided on the conductive base member 12 as shown in FIG. 5, and the charge generating layer 24 may be provided on the charge transfer layer 22. Since the charge generating layer 24 has a thinner film thickness compared with the charge transfer layer 22, however, it is preferable to provide the charge transfer layer 22 on the charge generating layer 24.

Moreover, examples of the conductive base member include those presented for the monolayer type photoconductor.

Moreover, the thickness of the charge generating layer is preferably 0.01 to 5 μm, and more preferably 0.1 to 3 μl.

Moreover, the thickness of the charge transfer layer is preferably 2 to 100 μm, and more preferably 5 to 50 μm.

Whether the multilayer type photoconductor is of the positive charge type or the negative charge type is selected depending on the formation order of the charge generating layer and the charge transfer layer, and the kind of the charge transfer agent to be used for the charge transfer layer. For example, in the case where a hole transfer agent such as the compound (1) is used as the charge transfer agent for the charge transfer layer in a multilayer type photoconductor having the charge generating layer on the conductive base member, and the charge transfer layer provided thereon, the photoconductor is of the negative charge type. In this case, the charge generating layer may contain an electron transfer agent.

Moreover, examples of the charge generating agent, the hole transfer agent, the electron transfer agent, the binding agent, and the like include those same as the monolayer type photoconductor.

Moreover, the content of the charge generating agent in the charge generating layer is preferably 5 to 1,000 parts by weight with respect to 100 parts by weight of the binding resin, and more preferably 30 to 500 parts by weight.

In the case the charge generating layer contains the hole transfer agent, the content of the hole transfer agent is preferably 10 to 500 parts by weight with respect to 100 parts by weight of the binding resin, and more preferably 50 to 200 parts by weight.

It is also preferable that the content of the hole transfer agent including a specific diphenyl amine derivative is 10 to 500 parts by weight with respect to 100 parts by weight of the binding resin of the charge transfer layer included in the photoconductor layer.

The reason thereof is that by providing the content of the hole transfer agent including a specific diphenyl amine derivative in a value in such a range, an electrophotographic photoconductor having a still better sensitivity can be obtained by further improving the dispersibility in the charge transfer layer of the specific diphenyl amine derivative.

That is, if the content of the specific diphenyl amine derivative is of a value of below 10 parts by weight, the sensitivity is lowered so as to generate a trouble in the practical use. If the content of such a specific diphenyl amine derivative is of a value of above 500 parts by weight, on the other hand, crystallization of the specific diphenyl amine derivative is excessively facilitated so that the photoconductor layer may hardly be formed adequately.

Therefore, it is more preferable that the content of such a specific diphenyl amine derivative is of a value in a range of 25 to 200 parts by weight.

In the case the electron transfer agent is contained in the charge transfer layer, the content of the electron transfer agent is preferably 5 to 200 parts by weight with respect to 100 parts by weight of the binding resin, and more preferably 10 to 100 parts by weight.

The charge generating layer is formed by means of for example, vapor deposition or coating.

Moreover, the charge transfer layer is formed by means of coating, or the like in the same manner as the photoconductor layer of the monolayer type photoconductor.

EXAMPLES

Hereinafter, the present invention will be explained in further details with reference to Examples.

Compounds (4-1) to (4-4) were produced by different preparation steps as follows.

Production Example 1

Production of Compound (4-1)

Step (a-1)

20 g (0.124 mol) of a compound (7-1) and 30 g (0.181 mol) of a triethyl phosphite were placed in a 200 mL flask so as to be agitated for 8 hours while being heated at 180° C. After cooling down to the room temperature, an excessive triethyl phosphite ester was removed under reduced pressure so as to obtain 29.3 g of a compound (8-1) (yield rate 90%).

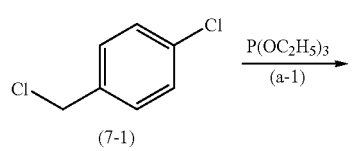

(7-1)

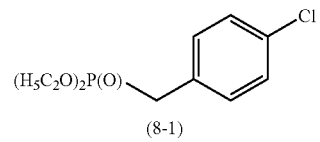

(8-1)

Step (b-1)

Then, with 13 g (0.049 mol) of a compound (8-1) placed in a 500 mL branched-neck flask and argon gas substitution, 100 mL of a dried tetrahydrofuran (THF) and 15.2 g (0.079 mol) of a 28% sodium methoxide were added so as to be agitated for 30 minutes at 0° C. Then, 6 g (0.057 mol) of a compound (9-1) dissolved in 300 mL of a dried THF was added to the reaction solution so as to be agitated for 12 hours at the room temperature. Thereafter, the reaction solution was poured into ion exchange water and extracted with a toluene, and the organic layer was washed with ion exchange water for 5 times. Then, after drying the organic layer with a sodium sulfate anhydride, the solvent was removed. Thereafter, the residue was refined by re-crystallization with a solvent mixture of 20 mL of a toluene/100 mL of a methanol to obtain 10.7 g of a compound (4-1) (yield rate 88%).

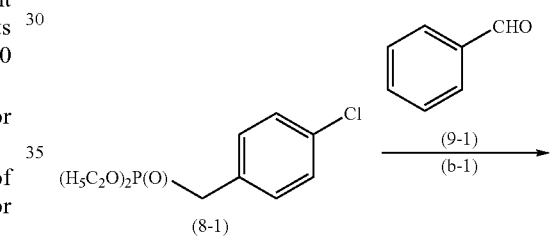

(8-1) (9-1) (b-1)

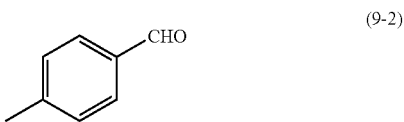

(4-1)

Production Example 2

Production of Compound (4-2)

9.3 g of a compound (4-2) was obtained (yield rate 85%) in the same manner as in Production example 1 except that 6.7 g (0.057 mol) of a compound (9-2) was used instead of the compound (9-1) in step (b-1).

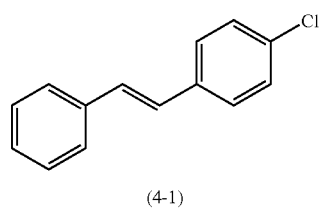

(9-2)

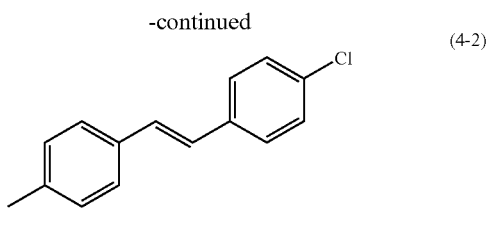

(4-2)

Production Example 3

Production of Compound (4-3)

Step (a-2)

19 g (0.124 mol) of a compound (10-1) and 30 g (0.181 mol) of a triethyl phosphite were placed in a 200 mL flask so as to be agitated for 8 hours while being heated at 180° C. After cooling down to the room temperature, an excessive triethyl phosphite ester was removed under reduced pressure so as to obtain 28.6 g of a compound (11-1) (yield rate 86%).

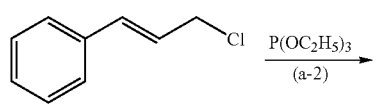

Step (b-2)

Then, with 14.3 g (0.05 mol) of a compound (11-1) placed in a 500 mL branched-neck flask and argon gas substitution, 100 mL of a dried tetrahydrofuran (THF) and 15.2 g (0.079 mol) of a 28% sodium methoxide were added so as to be agitated for 30 minutes at 0° C. Then, 7 g (0.05 mol) of a compound (12-1) dissolved in 300 mL of a dried THF was added to the reaction solution so as to be agitated for 12 hours at the room temperature. Thereafter, the reaction solution was poured into ion exchange water and extracted with a toluene, and the organic layer was washed with ion exchange water for 5 times. Then, after drying the organic layer with a sodium sulfate anhydride, the solvent was removed. Thereafter, the residue was refined by re-crystallization with a solvent mixture of 20 mL of a toluene/100 mL of a methanol to obtain 9.9 g of a compound (4-3) (yield rate 82%).

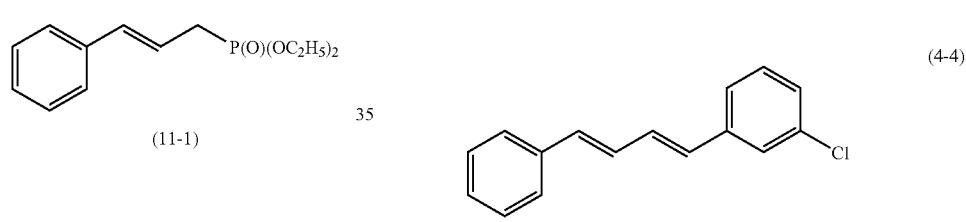

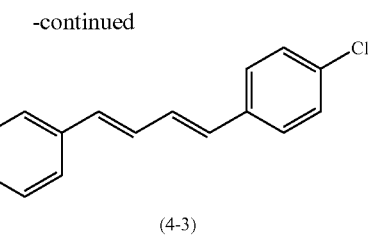

(4-3)

Production Example 4

Production of Compound (4-4)

9.6 g of a compound (4-4) was obtained (yield rate 80%) in the same manner as in Production example 3 except that a compound (12-2) was used instead of the compound (12-1) in step (b-1)

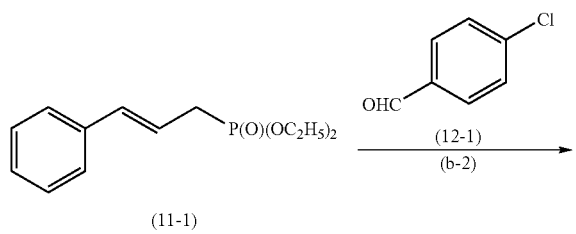

Example 1

Production of Compound (1-1)

Step (A)

With 7.3 g (0.034 mol) of a compound (4-1), 0.07 g (0.2 mmol) of a (2-biphenyl) dicyclohexyl phosphine, 0.1 g (0.1 mmol) of a tris (dibendilidene acetone) dipalladium (0), 5 g (0.05 mol) of a sodium-tert-butoxide, and 2.57 g (0.017 mol) of a compound (3-1) placed in a 2 L branched-neck flask, 500 mL of o-xylene was added, and the argon gas substitution was carried out so as to be agitated for 3 hours while being heated at 120° C. After cooling down to the room temperature, the organic layer was washed with ion exchange water for 3 times, and a drying and adsorption process was applied to the organic layer using a sodium sulfide anhydride and active white clay, and xylene was removed under reduced pressure. Finally, the residue was refined by the column chromatography (developing solvent: chloroform/hexane) to obtain 7.4 g of a compound (1-1) (yield rate 86%).

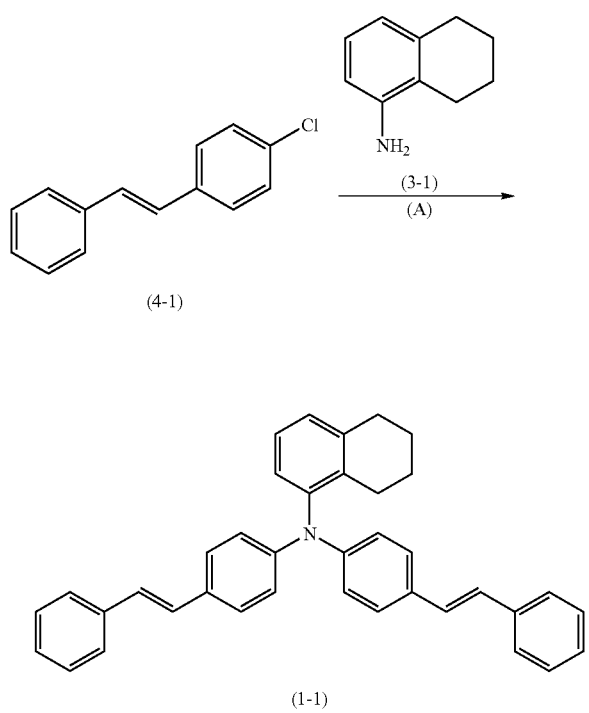

(Solubility Evaluation)

The solubility of the obtained compound (1-1) was evaluated.

That is, the sample was added to a tetrahydrofuran so as to have a 25% by mass concentration for confirming the solubility by the visual observation for evaluation according to the following criteria. The obtained results are shown in Table 1.

○ (good): The solution was transparent.

Δ (fair): The sample remained slightly without being dissolved.

X (bad): The sample remained without being dissolved with the solution being opaque.

(Production of Electrophotographic Photoconductor)

A monolayer type photoconductor layer application liquid was prepared by mixing and dispersing 5 parts by weight of a X type non metal phthalocyanine as the charge generating agent, 80 parts by weight of the compound (1-1) as the hole transfer agent, 50 parts by weight of the compound (13-1) as the electron transfer agent, and 100 parts by weight of a siloxane component containing polycarbonate resin as the binding resin in 800 parts by weight of a tetrahydrofuran as the solvent with a ball mill for 50 hours. Then, by applying the application liquid onto a conductive base member including an aluminum bare pipe by the dip coat method, and hot air drying at 100° C. for 30 minutes, a 25 μm film thickness photoconductor layer was formed so as to obtain a monolayer type photoconductor.

(Electric Characteristic Evaluation)

Then, with the monolayer type photoconductor installed on a drum sensitivity tester produced by GENTEC Corp., the monolayer type photoconductor was charged so as to have the initial surface potential $V_0$ of +700 V. Then, a monochrome light beam (light intensity 1.5 μJ/cm$^2$) of a 780 nm wavelength (half value width 20 nm) taken out from a white light beam of a halogen lamp using a band pass filter was directed to the surface of the monolayer type photoconductor for 1.5 seconds for measuring the surface potential at the time 0.5 second was passed from starting the exposure, and it was provided as the residual potential $V_L$ (V). The obtained results are shown in Table 2.

(Evaluation of the Photoconductor External Appearance)

Moreover, the photoconductor layer surface of the monolayer type photoconductor was observed for evaluation according to the following criteria. The obtained results are shown in Table 2.

○ (good): Crystallization was not observed.

Δ (fair): Crystallization was slightly observed.

X (bad): Crystallization was observed.

Example 2

A monolayer type photoconductor was produced and evaluated in the same manner as in Example 1 except that a compound (13-3) was used instead of the compound (13-1) as the electron transfer agent. The obtained results are shown in Table 2.

Example 3

A monolayer type photoconductor was produced and evaluated in the same manner as in Example 2 except that a Y type titanyl phthalocyanine was used instead of the X type non metal phthalocyanine as the charge generating agent. The obtained results are shown in Table 2.

Example 4

Production of Compound (1-2)

7.7 g of a compound (1-2) was obtained (yield rate 85%) in the same manner as in Example 1 except that 7.8 g (0.034 mol) of a compound (4-2) was used instead of the compound (4-1) in step (A).

Moreover, the solubility of the compound (1-2) was also evaluated. The obtained results are shown in Table 1.

Figure 6:
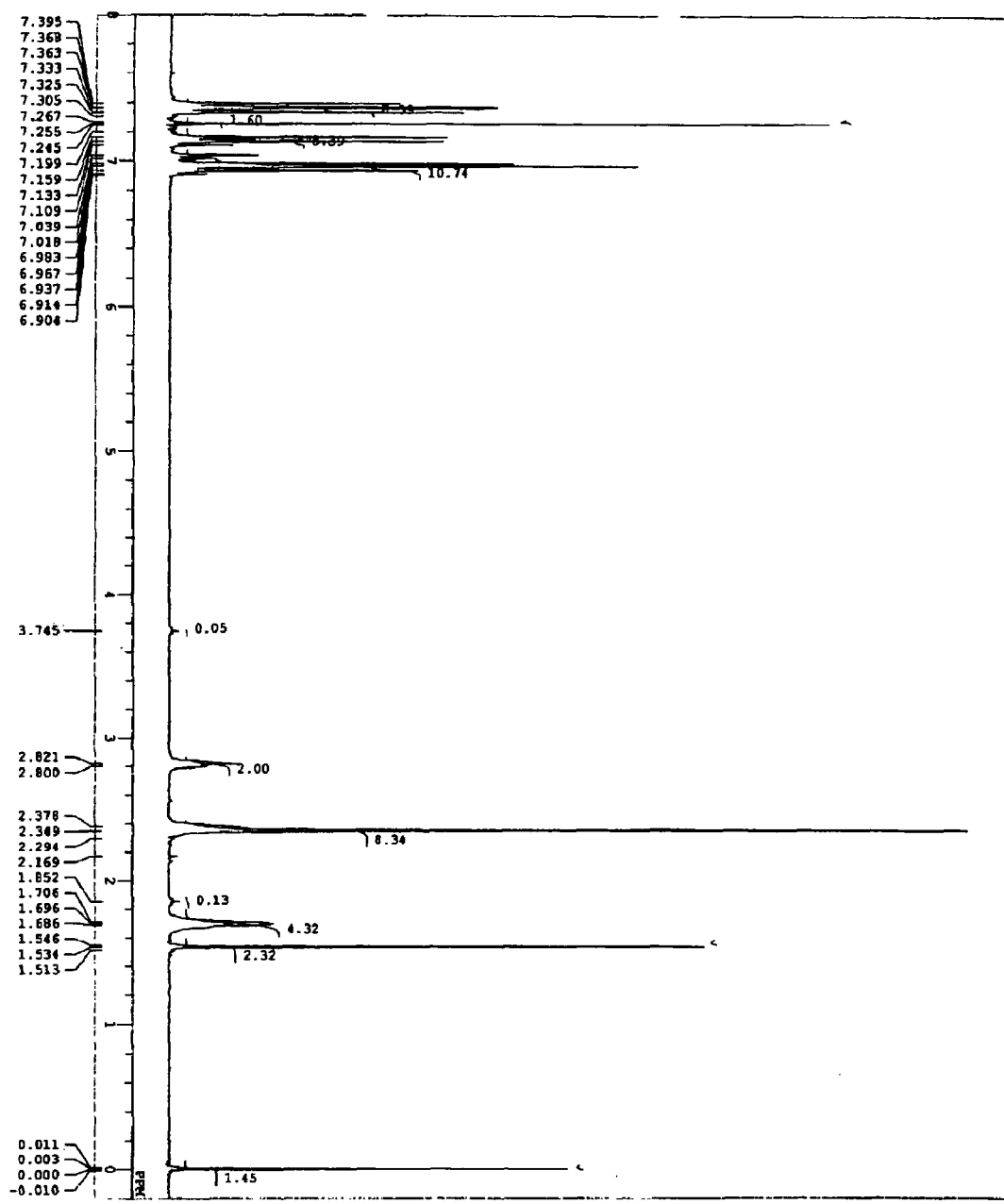
FIG. 6 is a $^1$H-NMR chart of a compound (1-2)

Furthermore, the $^1$H-NMR (300 MHz) was measured for the compound (1-2). A CDCl$_3$ was used as the solvent, and a TMS was used as the reference substance. Obtainment of the compound (1-2) was confirmed. A $^1$H-NMR chart is shown in FIG. 6.

(Production of Electrophotographic Photoconductor)

A monolayer type photo conductor was produced and evaluated in the same manner as in Example 1 except that a compound (1-2) was used instead of the compound (1-1) as the hole transfer agent at the time of producing the electrophotographic photoconductor. The obtained results are shown in Table 2.

Example 5

A monolayer type photoconductor was produced and evaluated in the same manner as in Example 4 except that a compound (13-3) was used instead of the compound (13-1) as the electron transfer agent at the time of producing the electrophotographic photoconductor. The obtained results are shown in Table 2.

Example 6

A monolayer type photoconductor was produced and evaluated in the same manner as in Example 5 except that a Y type titanyl phthalocyanine was used instead of the X type non metal phthalocyanine as the charge generating agent at the time of producing the electrophotographic photoconductor. The obtained results are shown in Table 2.

Example 7

Production of Compound (1-3)

8 g of a compound (1-3) was obtained (yield rate 85%) in the same manner as in Example 1 except that 8.2 g (0.034 mol) of a compound (4-3) was used instead of the compound (4-1) in step (A).

Moreover, the solubility of the compound (1-3) was evaluated. The obtained results are shown in Table 1.

Figure 7:
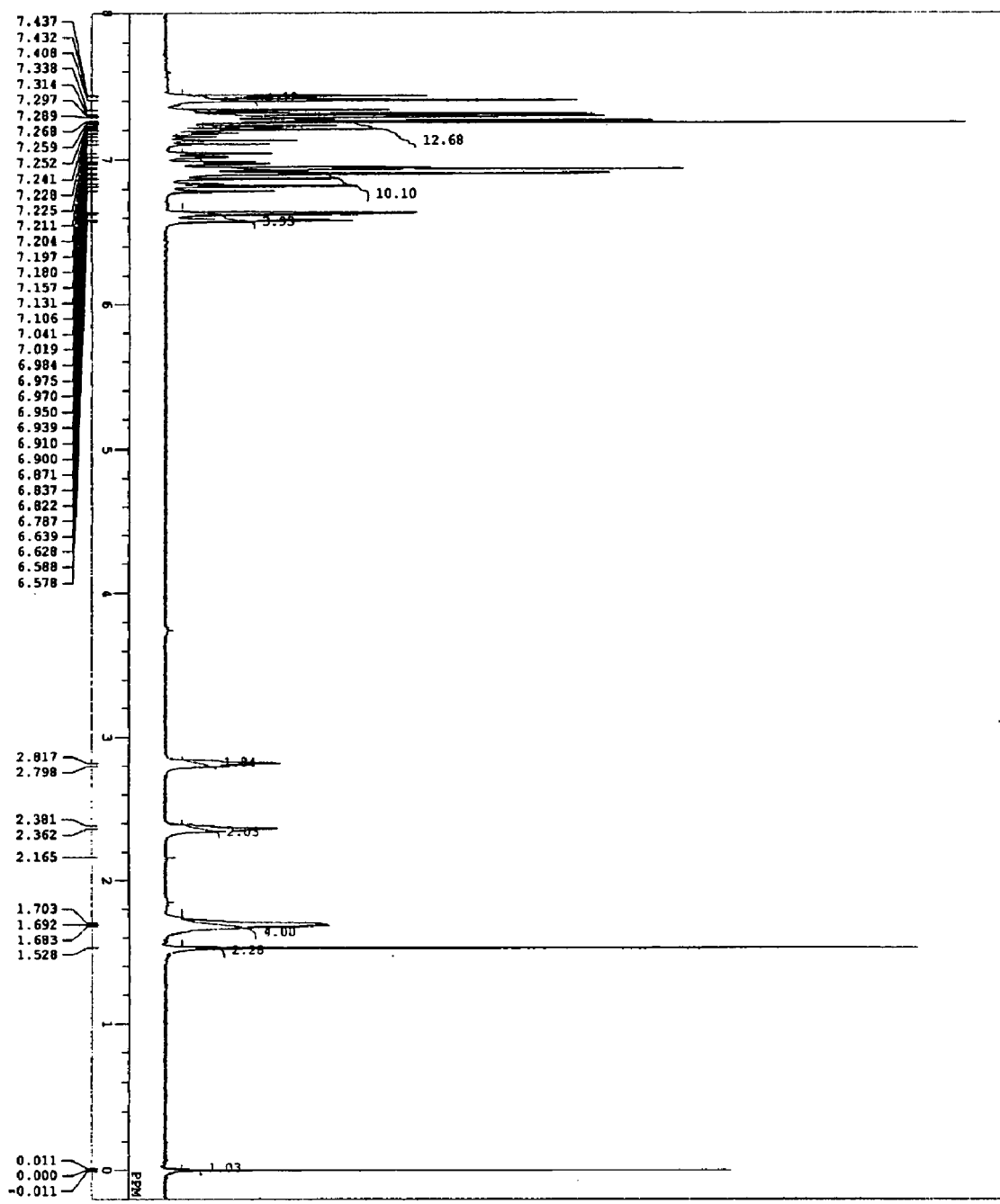
FIG. 7 is a $^1$H-NMR chart of a compound (1-3)

Furthermore, the $^1$H-NMR (300 MHz) was measured for the compound (1-3). A CDCl$_3$ was used as the solvent, and a TMS was used as the reference substance. Obtainment of the compound (1-3) was confirmed. A $^1$H-NMR chart is shown in FIG. 7.

(Production of Electrophotographic Photoconductor)

A monolayer type photoconductor was produced and evaluated in the same manner as in Example 1 except that a compound (1-3) was used instead of the compound (1-1) as the hole transfer agent at the time of producing the electrophotographic photoconductor. The obtained results are shown in Table 2.

Example 8

A monolayer type photoconductor was produced and evaluated in the same manner as in Example 7 except that a compound (13-3) was used instead of the compound (13-1) as the electron transfer agent at the time of producing the electrophotographic photoconductor. The obtained results are shown in Table 2.

Example 9

A monolayer type photoconductor was produced and evaluated in the same manner as in Example 8 except that a Y type titanyl phthalocyanine was used instead of the X type non metal phthalocyanine as the charge generating agent at the time of producing the electrophotographic photoconductor. The obtained results are shown in Table 2.

Example 10

Production of Compound (1-4)

Step (A)

With 18.3 g (0.076 mol) of a compound (4-3), 0.066 g (0.00019 mol) of a (2-biphenyl) dicyclohexyl phosphine, 0.086 g (0.000094 mol) of a tris (dibendilidene acetone) dipalladium (0), 7.68 g (0.080 mol) of a sodium-tert-butoxide, and 11.2 g (0.076 mol) of a compound (3-1) placed in a 2 L branched-neck flask, 500 mL of o-xylene was added, and the argon gas substitution was carried out so as to be agitated for 5 hours while being heated at 120° C. After cooling down to the room temperature, the organic layer was washed with ion exchange water for 3 times, and a drying and adsorption process was applied to the organic layer using a sodium sulfide anhydride and active white clay, and xylene was removed under reduced pressure. Finally, the residue was refined by the column chromatography (developing solvent: chloroform/hexane) to obtain 21.7 g of a compound (5-1) (yield rate 85%).

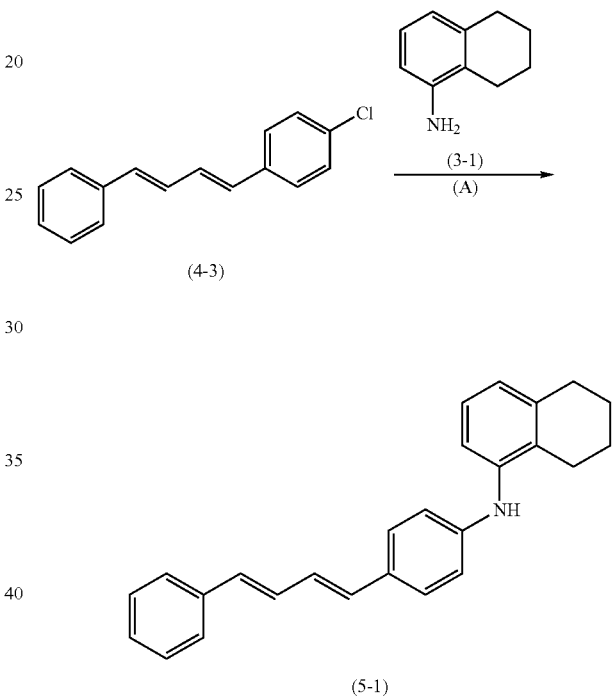

Step (B)

Then, with 4.3 g (0.018 mol) of a compound (4-4), 0.016 g (0.000045 mol) of a (2-biphenyl) dicyclohexyl phosphine, 0.021 g (0.000023 mol) of a tris (dibendilidene acetone) dipalladium (O), 2.88 g (0.030 mol) of a sodium-tert-butoxide, and 6.1 g (0.018 mol) of a compound (5-1) placed in a 300 mL branched-neck flask, 500 mL of o-xylene was added, and the argon gas substitution was carried out so as to be agitated for 3 hours while being heated at 120° C. After cooling down to the room temperature, the organic layer was washed with ion exchange water for 3 times, and a drying and adsorption process was applied to the organic layer using a sodium sulfide anhydride and active white clay, and xylene was removed under reduced pressure. Finally, the residue was refined by the column chromatography (developing solvent: chloroform/hexane) to obtain 8.3 g of a compound (1-4) (yield rate 83%).

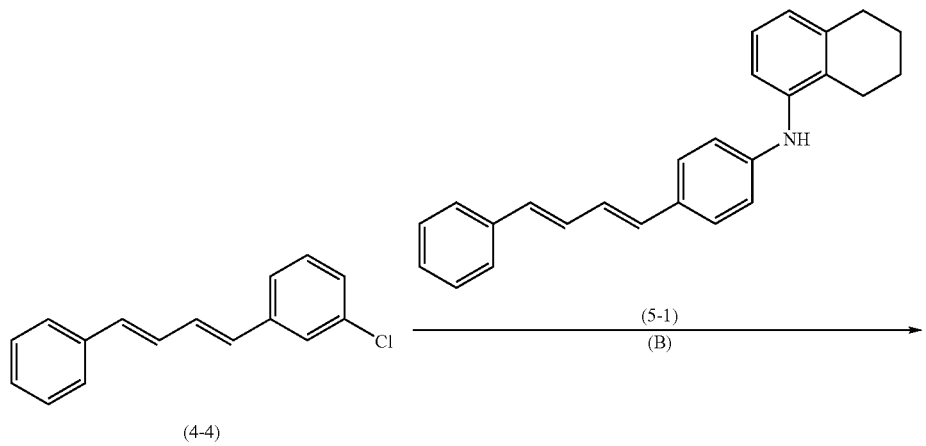

(4-4)     (5-1) (B) →

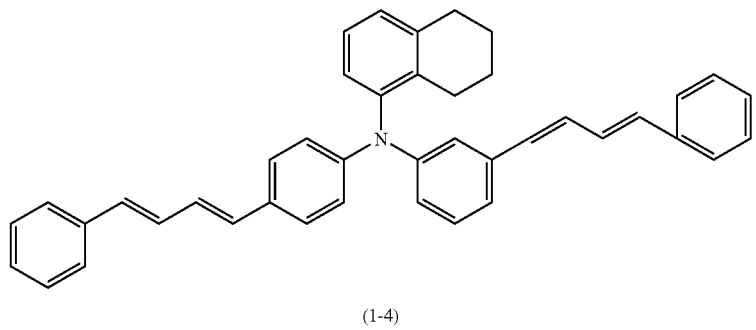

(1-4)

Moreover, the solubility of the compound (1-4) was evaluated. The obtained results are shown in Table 1.

(Production of Electrophotographic Photoconductor)

A mono layer type photo conductor was produced and evaluated in the same manner as in Example 1 except that a compound (1-4) was used instead of the compound (1-1) as the hole transfer agent at the time of producing the electrophotographic photoconductor. The obtained results are shown in Table 2.

Example 11

A monolayer type photoconductor was produced and evaluated in the same manner as in Example 10 except that a compound (13-3) was used instead of the compound (13-1) as the electron transfer agent at the time of producing the electrophotographic photoconductor. The obtained results are shown in Table 2.

Example 12

A monolayer type photoconductor was produced and evaluated in the same manner as in Example 11 except that a Y type titanyl phthalocyanine was used instead of the X type non metal phthalocyanine as the charge generating agent at the time of producing the electrophotographic photoconductor. The obtained results are shown in Table 2.

Example 13

Production of Compound (1-5)

8.3 g of a compound (1-5) was obtained (yield rate 83%) in the same manner as in Example 7 except that a compound (3-2) was used instead of the compound (3-1) in step (A).

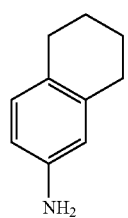

(3-2)

Moreover, the solubility of the compound (1-5) was evaluated. The obtained results are shown in Table 1.

(Production of Electrophotographic Photoconductor)

A monolayer type photoconductor was produced and evaluated in the same manner as in Example 1 except that a compound (1-5) was used instead of the compound (1-1) as the hole transfer agent at the time of producing the electrophotographic photoconductor. The obtained results are shown in Table 2.

Example 14

A monolayer type photoconductor was produced and evaluated in the same manner as in Example 13 except that a compound (13-3) was used instead of the compound (13-1) as the electron transfer agent at the time of producing the electrophotographic photoconductor. The obtained results are shown in Table 2.

Example 15

A monolayer type photoconductor was produced and evaluated in the same manner as in Example 14 except that a Y type titanyl phthalocyanine was used instead of the X type non metal phthalocyanine as the charge generating agent at the time of producing the electrophotographic photoconductor. The obtained results are shown in Table 2.

Example 16

Production of Compound (1-6)

7.6 g of a compound (1-6) was obtained (yield rate 80%) in the same manner as in Example 10 except that 3.8 g (0.018 mol) of a compound (4-1) was used instead of the compound (4-4) in step (B).

Moreover, the solubility of the compound (1-6) was evaluated. The obtained results are shown in Table 1.

(Production of Electrophotographic Photoconductor)

A monolayer type photoconductor was produced and evaluated in the same manner as in Example 1 except that a compound (1-6) was used instead of the compound (1-1) as the hole transfer agent at the time of producing the electrophotographic photoconductor. The obtained results are shown in Table 2.

Example 17

A monolayer type photoconductor was produced and evaluated in the same manner as in Example 16 except that a compound (13-3) was used instead of the compound (13-1) as the electron transfer agent at the time of producing the electrophotographic photoconductor. The obtained results are shown in Table 2.

Example 18

A monolayer type photoconductor was produced and evaluated in the same manner as in Example 17 except that a Y type titanyl phthalocyanine was used instead of the X type non metal phthalocyanine as the charge generating agent at the time of producing the electrophotographic photoconductor. The obtained results are shown in Table 2.

Example 19

Production of Compound (1-7)

7.8 g of a compound (1-7) was obtained (yield rate 82%) in the same manner as in Example 16 except that a compound (3-2) was used instead of the compound (3-1) in step (A).

Moreover, the solubility of the compound (1-7) was evaluated. The obtained results are shown in Table 1.

(Production of Electrophotographic Photoconductor)

A monolayer type photo conductor was produced and evaluated in the same manner as in Example 1 except that a compound (1-7) was used instead of the compound (1-1) as the hole transfer agent at the time of producing the electrophotographic photoconductor. The obtained results are shown in Table 2.

Example 20

A monolayer type photoconductor was produced and evaluated in the same manner as in Example 19 except that a compound (13-3) was used instead of the compound (13-1) as the electron transfer agent at the time of producing the electrophotographic photoconductor. The obtained results are shown in Table 2.

Example 21

A monolayer type photoconductor was produced and evaluated in the same manner as in Example 20 except that a Y type titanyl phthalocyanine was used instead of the X type non metal phthalocyanine as the charge generating agent at the time of producing the electrophotographic photoconductor. The obtained results are shown in Table 2.

Example 22

Production of Compound (1-8)

7.8 g of a compound (1-8) was obtained (yield rate 79%) in the same manner as in Example 10 except that 4.1 g (0.018 mol) of a compound (4-2) was used instead of the compound (4-4) in step (B).

Moreover, the solubility of the compound (1-8) was evaluated. The obtained results are shown in Table 1.

Figure 8:
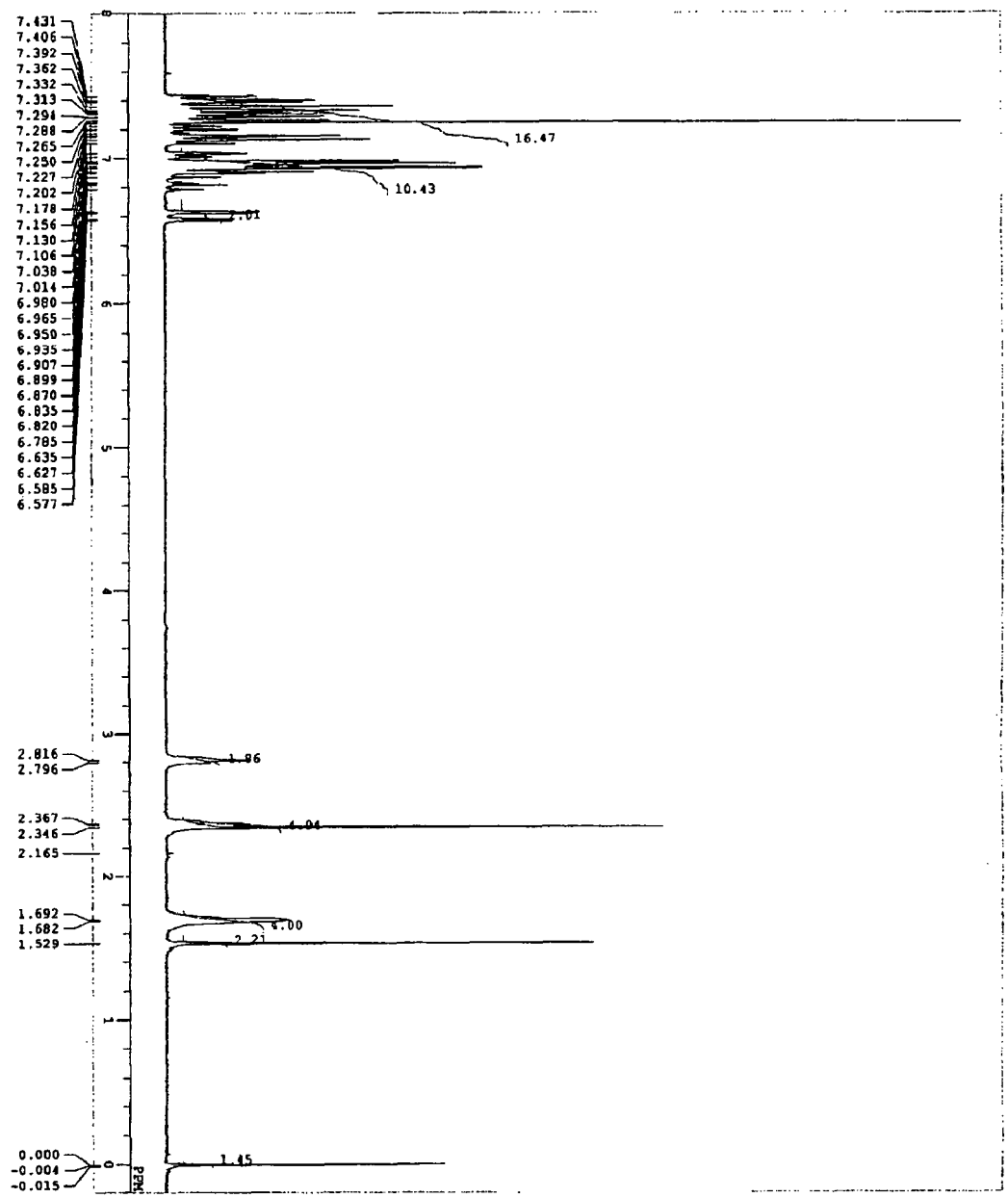
FIG. 8 is a $^1$H-NMR chart of a compound (1-8).

Furthermore, the $^1$H-NMR (300 MHz) was measured for the compound (1-8). A $CDCl_3$ was used as the solvent and a TMS was used as the reference substance. Obtainment of the compound (1-8) was confirmed. A $^1$H-NMR chart is shown in FIG. 8.

(Production of Electrophotographic Photoconductor)

A monolayer type photoconductor was produced and evaluated in the same manner as in Example 1 except that a compound (1-8) was used instead of the compound (1-1) as the hole transfer agent at the time of producing the electrophotographic photoconductor. The obtained results are shown in Table 2.

Example 23

A monolayer type photoconductor was produced and evaluated in the same manner as in Example 22 except that a compound (13-3) was used instead of the compound (13-1) as the electron transfer agent at the time of producing the electrophotographic photoconductor. The obtained results are shown in Table 2.

Example 24

A monolayer type photoconductor was produced and evaluated in the same manner as in Example 23 except that a Y type titanyl phthalocyanine was used instead of the X type non metal phthalocyanine as the charge generating agent at the time of producing the electrophotographic photoconductor. The obtained results are shown in Table 2.

Example 25

Production of Compound (1-9)

15.2 g of a compound (1-9) was obtained (yield rate 83%) in the same manner as in Example 7 except that a compound (3-3) was used instead of the compound (3-1) in step (A).

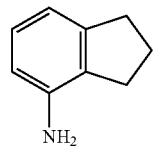

(3-3)

Moreover, the solubility of the compound (1-9) was evaluated. The obtained results are shown in Table 1.

(Production of Electrophotographic Photoconductor)

A monolayer type photoconductor was produced and evaluated in the same manner as in Example 1 except that a compound (1-9) was used instead of the compound (1-1) as the hole transfer agent at the time of producing the electrophotographic photoconductor. The obtained results are shown in Table 2.

Example 26

A monolayer type photoconductor was produced and evaluated in the same manner as in Example 25 except that a compound (13-3) was used instead of the compound (13-1) as the electron transfer agent at the time of producing the electrophotographic photoconductor. The obtained results are shown in Table 2.

Example 27

A mono layer type photoconductor was produced and evaluated in the same manner as in Example 26 except that a Y type titanyl phthalocyanine was used instead of the X type non metal phthalocyanine as the charge generating agent at the time of producing the electrophotographic photoconductor. The obtained results are shown in Table 2.

Example 28

Production of Compound (1-10)

15.3 g of a compound (1-10) was obtained (yield rate 85%) in the same manner as in Example 22 except that a compound (3-3) was used instead of the compound (3-1) in step (A).

Moreover, the solubility of the compound (1-9) was evaluated. The obtained results are shown in Table 1.

(Production of Electrophotographic Photoconductor)

A monolayer type photoconductor was produced and evaluated in the same manner as in Example 1 except that a compound (1-10) was used instead of the compound (1-1) as the hole transfer agent at the time of producing the electrophotographic photoconductor. The obtained results are shown in Table 2.

Example 29

A monolayer type photoconductor was produced and evaluated in the same manner as in Example 28 except that a compound (13-3) was used instead of the compound (13-1) as the electron transfer agent at the time of producing the electrophotographic photoconductor. The obtained results are shown in Table 2.

Example 30

A monolayer type photoconductor was produced and evaluated in the same manner as in Example 29 except that a Y type titanyl phthalocyanine was used instead of the X type non metal phthalocyanine as the charge generating agent at the time of producing the electrophotographic photoconductor. The obtained results are shown in Table 2.

Example 31

Production of Compound (1-11)

15.8 g of a compound (1-11) was obtained (yield rate 85%) in the same manner as in Example 7 except that a compound (3-4) was used instead of the compound (3-1) in step (A).

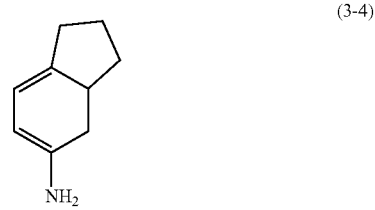

(3-4)

Moreover, the solubility of the compound (1-11) was evaluated. The obtained results are shown in Table 1.

(Production of Electrophotographic Photoconductor)

A monolayer type photoconductor was produced and evaluated in the same manner as in Example 1 except that a compound (1-11) was used instead of the compound (1-1) as the hole transfer agent at the time of producing the electrophotographic photoconductor. The obtained results are shown in Table 2.

Example 32

A monolayer type photoconductor was produced and evaluated in the same manner as in Example 31 except that a compound (13-3) was used instead of the compound (13-1) as the electron transfer agent at the time of producing the electrophotographic photoconductor. The obtained results are shown in Table 2.

Example 33

A monolayer type photoconductor was produced and evaluated in the same manner as in Example 32 except that a Y type titanyl phthalocyanine was used instead of the X type non metal phthalocyanine as the charge generating agent at the time of producing the electrophotographic photoconductor. The obtained results are shown in Table 2.

Example 34

Production of Compound (1-12)

15.5 g of a compound (1-12) was obtained (yield rate 86%) in the same manner as in Example 22 except that a compound (3-4) was used instead of the compound (3-1) in step (A).

Moreover, the solubility of the compound (1-12) was evaluated. The obtained results are shown in Table 1.

(Production of Electrophotographic Photoconductor)

A monolayer type photoconductor was produced and evaluated in the same manner as in Example 1 except that a compound (1-12) was used instead of the compound (1-1) as the hole transfer agent at the time of producing the electrophotographic photoconductor. The obtained results are shown in Table 2.

Example 35

A monolayer type photoconductor was produced and evaluated in the same manner as in Example 34 except that a compound (13-3) was used instead of the compound (13-1) as the electron transfer agent at the time of producing the electrophotographic photoconductor. The obtained results are shown in Table 2.

Example 36

A monolayer type photoconductor was produced and evaluated in the same manner as in Example 35 except that a Y type titanyl phthalocyanine was used instead of the X type non metal phthalocyanine as the charge generating agent at the time of producing the electrophotographic photoconductor. The obtained results are shown in Table 2.

Comparative Examples 1 to 3

First, the solubility of the compound (6-1) was evaluated. The obtained results are shown in Table 1.

Moreover, a monolayer type photoconductor was produced and evaluated in the same manner as in Examples 1 to 3 except that a compound (6-1) was used instead of the compound (1-1) as the hole transfer agent at the time of producing the electrophotographic photoconductor. The obtained results are shown in Table 2.

Comparative Examples 4 to 6

Similarly, the solubility of the compound (6-2) was evaluated. The obtained results are shown in Table 1.

Moreover, a monolayer type photoconductor was produced in the same manner as in Examples 1 to 3 except that a compound (6-2) was used instead of the compound (1-1) as the hole transfer agent at the time of producing the electrophotographic photoconductor. However, since the compound (6-2) was crystallized after applying the application liquid onto the conductive base member and drying, it cannot be evaluated.

TABLE 1

| Hole transfer agent | Solubility |
|---|---|
| (1-1) | ○ (good) |
| (1-2) | ○ (good) |
| (1-3) | ○ (good) |
| (1-4) | ○ (good) |
| (1-5) | ○ (good) |
| (1-6) | ○ (good) |
| (1-7) | ○ (good) |
| (1-8) | ○ (good) |
| (1-9) | ○ (good) |
| (1-10) | ○ (good) |
| (1-11) | ○ (good) |
| (1-12) | ○ (good) |
| (6-1) | Δ (fair) |
| (6-2) | X (bad) |

TABLE 2

| | Charge generating agent | Hole transfer agent | Electron transfer agent | $V_0$ (V) | $V_L$ (V) | appearance |
|---|---|---|---|---|---|---|
| Example 1 | X type non metal phthalocyanine | (1-1) | (13-1) | 700 | 125 | ○(good) |
| Example 2 | X type non metal phthalocyanine | (1-1) | (13-3) | 701 | 127 | ○(good) |
| Example 3 | Y type titanyl phthalocyanine | (1-1) | (13-3) | 701 | 120 | ○(good) |
| Example 4 | X type non metal phthalocyanine | (1-2) | (13-1) | 699 | 124 | ○(good) |
| Example 5 | X type non metal phthalocyanine | (1-2) | (13-3) | 700 | 126 | ○(good) |
| Example 6 | Y type titanyl phthalocyanine | (1-2) | (13-3) | 702 | 120 | ○(good) |
| Example 7 | X type non metal phthalocyanine | (1-3) | (13-1) | 698 | 114 | ○(good) |
| Example 8 | X type non metal phthalocyanine | (1-3) | (13-3) | 699 | 118 | ○(good) |
| Example 9 | Y type titanyl phthalocyanine | (1-3) | (13-3) | 700 | 108 | ○(good) |
| Example 10 | X type non metal phthalocyanine | (1-4) | (13-1) | 698 | 124 | ○(good) |
| Example 11 | X type non metal phthalocyanine | (1-4) | (13-3) | 699 | 126 | ○(good) |
| Example 12 | Y type titanyl phthalocyanine | (1-4) | (13-3) | 700 | 120 | ○(good) |
| Example 13 | X type non metal phthalocyanine | (1-5) | (13-1) | 698 | 120 | ○(good) |
| Example 14 | X type non metal phthalocyanine | (1-5) | (13-3) | 699 | 123 | ○(good) |
| Example 15 | Y type titanyl phthalocyanine | (1-5) | (13-3) | 700 | 114 | ○(good) |
| Example 16 | X type non metal phthalocyanine | (1-6) | (13-1) | 698 | 117 | ○(good) |
| Example 17 | X type non metal phthalocyanine | (1-6) | (13-3) | 699 | 119 | ○(good) |
| Example 18 | Y type titanyl phthalocyanine | (1-6) | (13-3) | 700 | 110 | ○(good) |
| Example 19 | X type non metal phthalocyanine | (1-7) | (13-1) | 698 | 122 | ○(good) |
| Example 20 | X type non metal phthalocyanine | (1-7) | (13-3) | 699 | 125 | ○(good) |
| Example 21 | Y type titanyl phthalocyanine | (1-7) | (13-3) | 700 | 117 | ○(good) |
| Example 22 | X type non metal phthalocyanine | (1-8) | (13-1) | 698 | 115 | ○(good) |
| Example 23 | X type non metal phthalocyanine | (1-8) | (13-3) | 699 | 117 | ○(good) |
| Example 24 | Y type titanyl phthalocyanine | (1-8) | (13-3) | 700 | 109 | ○(good) |
| Example 25 | X type non metal phthalocyanine | (1-9) | (13-1) | 700 | 116 | ○(good) |
| Example 26 | X type non metal phthalocyanine | (1-9) | (13-3) | 701 | 118 | ○(good) |
| Example 27 | Y type titanyl phthalocyanine | (1-9) | (13-3) | 701 | 110 | ○(good) |

TABLE 2-continued

| | Charge generating agent | Hole transfer agent | Electron transfer agent | $V_O(V)$ | $V_L(V)$ | appearance |
|---|---|---|---|---|---|---|
| Example 28 | X type non metal phthalocyanine | (1-10) | (13-1) | 699 | 120 | ○(good) |
| Example 29 | X type non metal phthalocyanine | (1-10) | (13-3) | 700 | 122 | ○(good) |
| Example 30 | Y type titanyl phthalocyanine | (1-10) | (13-3) | 702 | 113 | ○(good) |
| Example 31 | X type non metal phthalocyanine | (1-11) | (13-1) | 698 | 117 | ○(good) |
| Example 32 | X type non metal phthalocyanine | (1-11) | (13-3) | 699 | 119 | ○(good) |

Example 37

A monolayer type photoconductor was produced in the same manner as in Example 1 except that a compound (13-4) was used instead of the compound (13-1) as the electron transfer agent at the time of producing the electrophotographic photoconductor, and a Z type polycarbonate resin having a structure represented by the following formula (14) was used as the binding resin.

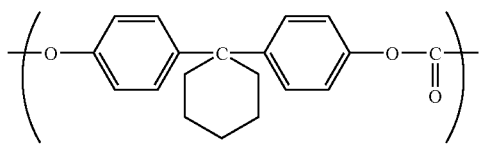

(14)

(Black Dot Generation Evaluation)

Then, with the obtained monolayer type photoconductor mounted on a printer (DP-560, produced by Kyocera Mita Corp.), 5,000 sheets of a A4 paper (high-quality PPC paper produced by Fuji Xerox Manufacturing Co. Ltd.) were printed continuously in a 40° C., 90 Rf environmental condition. Thereafter, after leaving for 6 hours, a blank A4 paper was printed for counting the number of generated black dots on the A4 paper and evaluated according to the following criteria. The obtained results are shown in Table 3.

⊚ (very good): Below 40 black dots generated per A4 paper sheet.

○ (good): 40 to below 50 black dots generated per A4 paper sheet.

Δ (fair): 50 to below 60 black dots generated per A4 paper sheet.

X (bad): Above 60 black dots generated per A4 paper sheet.

Example 38

A monolayer type photoconductor was produced and evaluated in the same manner as in Example 37 except that a Y type titanyl phthalocyanine was used instead of the X type non metal phthalocyanine as the charge generating agent at the time of producing the electrophotographic photoconductor. The obtained results are shown in Table 3.

Example 39

A monolayer type photoconductor was produced and evaluated in the same manner as in Example 37 except that a compound (1-2) was used instead of the compound (1-1) as the hole transfer agent at the time of producing the electrophotographic photoconductor. The obtained results are shown in Table 3.

Example 40

A monolayer type photoconductor was produced and evaluated in the same manner as in Example 39 except that a Y type titanyl phthalocyanine was used instead of the X type non metal phthalocyanine as the charge generating agent at the time of producing the electrophotographic photoconductor. The obtained results are shown in Table 3.

Example 41

A monolayer type photoconductor was produced and evaluated in the same manner as in Example 37 except that a compound (1-3) was used instead of the compound (1-1) as the hole transfer agent at the time of producing the electrophotographic photoconductor. The obtained results are shown in Table 3.

Example 42

A monolayer type photoconductor was produced and evaluated in the same manner as in Example 41 except that a Y type titanyl phthalocyanine was used instead of the X type non metal phthalocyanine as the charge generating agent at the time of producing the electrophotographic photoconductor. The obtained results are shown in Table 3.

Example 43

A monolayer type photoconductor was produced and evaluated in the same manner as in Example 37 except that a compound (1-4) was used instead of the compound (1-1) as the hole transfer agent at the time of producing the electrophotographic photoconductor. The obtained results are shown in Table 3.

Example 44

A monolayer type photoconductor was produced and evaluated in the same manner as in Example 43 except that a Y type titanyl phthalocyanine was used instead of the X type non metal phthalocyanine as the charge generating agent at the time of producing the electrophotographic photoconductor. The obtained results are shown in Table 3.

Example 45

A monolayer type photoconductor was produced and evaluated in the same manner as in Example 37 except that a compound (1-5) was used instead of the compound (1-1) as the hole transfer agent at the time of producing the electrophotographic photoconductor. The obtained results are shown in Table 3.

Example 46

A monolayer type photoconductor was produced and evaluated in the same manner as in Example 45 except that a Y type titanyl phthalocyanine was used instead of the X type non metal phthalocyanine as the charge generating agent at the time of producing the electrophotographic photoconductor. The obtained results are shown in Table 3.

Example 47

A monolayer type photoconductor was produced and evaluated in the same manner as in Example 37 except that a compound (1-6) was used instead of the compound (1-1) as the hole transfer agent at the time of producing the electrophotographic photoconductor. The obtained results are shown in Table 3.

Example 48

A monolayer type photoconductor was produced and evaluated in the same manner as in Example 47 except that a Y type titanyl phthalocyanine was used instead of the X type non metal phthalocyanine as the charge generating agent at the time of producing the electrophotographic photoconductor. The obtained results are shown in Table 3.

Example 49

A monolayer type photoconductor was produced and evaluated in the same manner as in Example 37 except that a compound (1-7) was used instead of the compound (1-1) as the hole transfer agent at the time of producing the electrophotographic photoconductor. The obtained results are shown in Table 3.

Example 50

A monolayer type photoconductor was produced and evaluated in the same manner as in Example 49 except that a Y type titanyl phthalocyanine was used instead of the X type non metal phthalocyanine as the charge generating agent at the time of producing the electrophotographic photoconductor. The obtained results are shown in Table 3.

Example 51

A monolayer type photoconductor was produced and evaluated in the same manner as in Example 37 except that a compound (1-8) was used instead of the compound (1-1) as the hole transfer agent at the time of producing the electrophotographic photoconductor. The obtained results are shown in Table 3.

Example 52

A monolayer type photoconductor was produced and evaluated in the same manner as in Example 51 except that a Y type titanyl phthalocyanine was used instead of the X type non metal phthalocyanine as the charge generating agent at the time of producing the electrophotographic photoconductor. The obtained results are shown in Table 3.

Example 53

A monolayer type photoconductor was produced and evaluated in the same manner as in Example 37 except that a compound (1-9) was used instead of the compound (1-1) as the hole transfer agent at the time of producing the electrophotographic photoconductor. The obtained results are shown in Table 3.

Example 54

A monolayer type photoconductor was produced and evaluated in the same manner as in Example 53 except that a Y type titanyl phthalocyanine was used instead of the X type non metal phthalocyanine as the charge generating agent at the time of producing the electrophotographic photoconductor. The obtained results are shown in Table 3.

Example 55

A monolayer type photoconductor was produced and evaluated in the same manner as in Example 37 except that a compound (1-10) was used instead of the compound (1-1) as the hole transfer agent at the time of producing the electrophotographic photoconductor. The obtained results are shown in Table 3.

Example 56

A monolayer type photoconductor was produced and evaluated in the same manner as in Example 55 except that a Y type titanyl phthalocyanine was used instead of the X type non metal phthalocyanine as the charge generating agent at the time of producing the electrophotographic photoconductor. The obtained results are shown in Table 3.

Example 57

A monolayer type photoconductor was produced and evaluated in the same manner as in Example 37 except that a compound (1-11) was used instead of the compound (1-1) as the hole transfer agent at the time of producing the electrophotographic photoconductor. The obtained results are shown in Table 3.

Example 58

A monolayer type photoconductor was produced and evaluated in the same manner as in Example 57 except that a Y type titanyl phthalocyanine was used instead of the X type non metal phthalocyanine as the charge generating agent at the time of producing the electrophotographic photoconductor. The obtained results are shown in Table 3.

Example 59

A monolayer type photoconductor was produced and evaluated in the same manner as in Example 37 except that a compound (1-12) was used instead of the compound (1-1) as the hole transfer agent at the time of producing the electrophotographic photoconductor. The obtained results are shown in Table 3.

Example 60

A monolayer type photoconductor was produced and evaluated in the same manner as in Example 59 except that a Y type titanyl phthalocyanine was used instead of the X type non metal phthalocyanine as the charge generating agent at the time of producing the electrophotographic photoconductor. The obtained results are shown in Table 3.

Comparative Example 7

A monolayer type photoconductor was produced and evaluated in the same manner as in Example 37 except that a compound (6-1) was used instead of the compound (1-1) as the hole transfer agent at the time of producing the electrophotographic photoconductor. The obtained results are shown in Table 3.

Comparative Example 8

A monolayer type photoconductor was produced and evaluated in the same manner as in Comparative example 7 except that a Y type titanyl phthalocyanine was used instead of the X type non metal phthalocyanine as the charge generating agent at the time of producing the electrophotographic photoconductor. The obtained results are shown in Table 3.

Comparative Example 9

A monolayer type photoconductor was produced and evaluated in the same manner as in Example 37 except that a compound (6-2) was used instead of the compound (1-1) as the hole transfer agent at the time of producing the electrophotographic photoconductor. The obtained results are shown in Table 3.

Comparative Example 10

A monolayer type photoconductor was produced and evaluated in the same manner as in Comparative example 9 except that a Y type titanyl phthalocyanine was used instead of the X type non metal phthalocyanine as the charge generating agent at the time of producing the electrophotographic photoconductor. The obtained results are shown in Table 3.

TABLE 3

| | Charge generating agent | Hole transfer agent | Electron transfer agent | Binding resin | Black dots (number) | Evaluation |
|---|---|---|---|---|---|---|
| Example 37 | X type non metal phthalocyanine | (1-1) | (13-4) | (PC-Z) | 38 | ⊚ (very good) |
| Example 38 | Y type titanyl phthalocyanine | (1-1) | (13-4) | (PC-Z) | 42 | ○ (good) |
| Example 39 | X type non metal phthalocyanine | (1-2) | (13-4) | (PC-Z) | 43 | ○ (good) |
| Example 40 | Y type titanyl phthalocyanine | (1-2) | (13-4) | (PC-Z) | 44 | ○ (good) |
| Example 41 | X type non metal phthalocyanine | (1-3) | (13-4) | (PC-Z) | 37 | ⊚ (very good) |
| Example 42 | Y type titanyl phthalocyanine | (1-3) | (13-4) | (PC-Z) | 40 | ○ (good) |
| Example 43 | X type non metal phthalocyanine | (1-4) | (13-4) | (PC-Z) | 44 | ○ (good) |
| Example 44 | Y type titanyl phthalocyanine | (1-4) | (13-4) | (PC-Z) | 46 | ○ (good) |
| Example 45 | X type non metal phthalocyanine | (1-5) | (13-4) | (PC-Z) | 40 | ○ (good) |
| Example 46 | Y type titanyl phthalocyanine | (1-5) | (13-4) | (PC-Z) | 42 | ○ (good) |
| Example 47 | X type non metal phthalocyanine | (1-6) | (13-4) | (PC-Z) | 42 | ○ (good) |
| Example 48 | Y type titanyl phthalocyanine | (1-6) | (13-4) | (PC-Z) | 42 | ○ (good) |
| Example 49 | X type non metal phthalocyanine | (1-7) | (13-4) | (PC-Z) | 43 | ○ (good) |
| Example 50 | Y type titanyl phthalocyanine | (1-7) | (13-4) | (PC-Z) | 45 | ○ (good) |
| Example 51 | X type non metal phthalocyanine | (1-8) | (13-4) | (PC-Z) | 43 | ○ (good) |
| Example 52 | Y type titanyl phthalocyanine | (1-8) | (13-4) | (PC-Z) | 45 | ○ (good) |
| Example 53 | X type non metal phthalocyanine | (1-9) | (13-4) | (PC-Z) | 40 | ○ (good) |
| Example 54 | Y type titanyl phthalocyanine | (1-9) | (13-4) | (PC-Z) | 40 | ○ (good) |
| Example 55 | X type non metal phthalocyanine | (1-10) | (13-4) | (PC-Z) | 43 | ○ (good) |
| Example 56 | Y type titanyl phthalocyanine | (1-10) | (13-4) | (PC-Z) | 41 | ○ (good) |
| Example 57 | X type non metal phthalocyanine | (1-11) | (13-4) | (PC-Z) | 41 | ○ (good) |
| Example 58 | Y type titanyl phthalocyanine | (1-11) | (13-4) | (PC-Z) | 42 | ○ (good) |
| Example 59 | X type non metal phthalocyanine | (1-12) | (13-4) | (PC-Z) | 43 | ○ (good) |
| Example 60 | Y type titanyl phthalocyanine | (1-12) | (13-4) | (PC-Z) | 45 | ○ (good) |
| Comparative example 7 | X type non metal phthalocyanine | (6-1) | (13-4) | (PC-Z) | 72 | X (bad) |

TABLE 3-continued

| | Charge generating agent | Hole transfer agent | Electron transfer agent | Binding resin | Black dots (number) | Evaluation |
|---|---|---|---|---|---|---|
| Comparative example 8 | Y type titanyl phthalocyanine | (6-1) | (13-4) | (PC-Z) | 75 | X(bad) |
| Comparative example 9 | X type non metal phthalocyanine | (6-2) | (13-4) | (PC-Z) | Not measurable | X(bad) |
| Comparative example 10 | Y type titanyl phthalocyanine | (6-2) | (13-4) | (PC-Z) | | X(bad) |

Since a diphenyl amine derivative of the present invention has the excellent solubility to a solvent and compatibility to a binding resin, an electrophotographic photoconductor having the excellent sensitivity, and capable of effectively restraining generation of the black dots can be obtained. Moreover, according to a production method for a diphenyl amine derivative of the present invention, a diphenyl amine derivative having a specific structure can be produced efficiently. Furthermore, an electrophotographic photoconductor of the present invention is expected to contribute to achievement of a high speed, a high performance, or the like in various image forming apparatus.

Since a diphenyl amine derivative of the present invention has a high hole transfer ability, it can be utilized also for a solar battery, an electroluminescence element, or the like.

What is claimed is:

1. A diphenyl amine derivative represented by the following general formula (1):

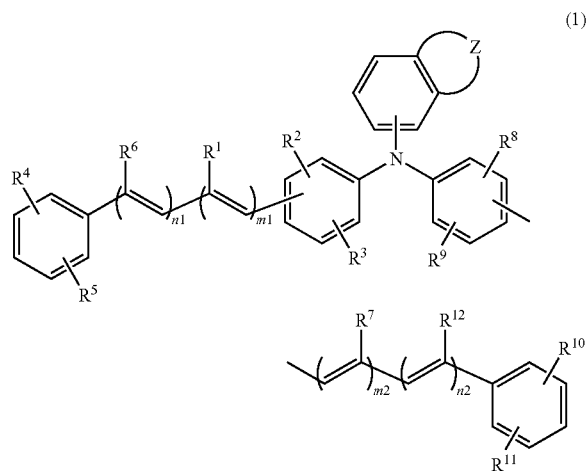

(In the general formula (1), $R^1$ to $R^{12}$ each are a hydrogen atom, an alkyl group which may have a substituent, an alkoxy group which may have a substituent, a phenoxy group which may have a substituent, an aryl group which may have a substituent, or an aralkyl group which may have a substituent, Z is a ring structure linked with a benzene ring, which is a 4 to 8-membered ring including a hydrogen atom, a nitrogen atom, an oxygen atom, a carbon atom or a sulfur atom, m1, m2, n1, n2 each are 0 or 1, m1+n1 is 1 or 2, and m2+n2 is 1 or 2), however neither m1+n1 nor m2+n2 become 1 at the same time, wherein a ring structure including a benzene ring in the diphenyl amine derivative represented by the general formula (1) is a structure represented by the following formula (2-1) or (2-2):

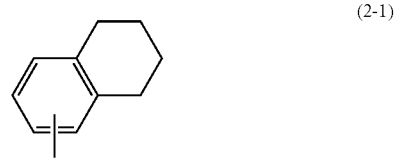

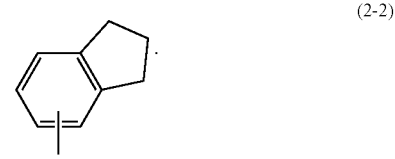

2. The diphenyl amine derivative according to claim 1, wherein when the ring structure including a benzene ring is represented by the formula (2-1), a nitrogen atom in the diphenyl amine derivative represented by the general formula (1) is bonded with the $5^{th}$ or $6^{th}$ place of the ring structure including a benzene ring, and when the ring structure including a benzene ring is represented by the formula (2-2), a nitrogen atom in the diphenyl amine derivative represented by the general formula (1) is bonded with the $4^{th}$ or $5^{th}$ place of the ring structure including a benzene ring.

3. The diphenyl amine derivative according to claim 1, wherein $R^1$ to $R^3$, $R^6$, $R^7$ to $R^9$ and $R^{12}$ in the general formula (I) are a hydrogen atom.

4. A production method for the diphenyl amine derivative according to claim 1, comprising the following steps (A) to (B):

(A) a step of obtaining a compound represented by the following general formula (5) by reacting a compound represented by the following general formula (3) with a compound represented by the general formula (4a); and (B) a step of obtaining a diphenyl amine derivative represented by the general formula (1) by reacting the obtained compound represented by the general formula (5) with a compound represented by the following general formula (4b):

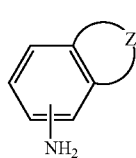

(3)

(In the general formula (3), Z is a ring structure linked to a benzene ring, which is a 4 to 8-membered ring including a hydrogen atom, a nitrogen atom, an oxygen atom, a carbon atom or a sulfur atom);

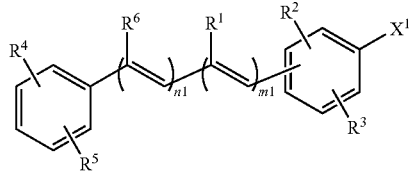

(4a)

(In the general formula (4a), $R^1$ to $R^6$ each are a hydrogen atom, an alkyl group which may have a substituent, an alkoxy group which may have a substituent, a phenoxy group which may have a substituent, an aryl group which may have a substituent, or an aralkyl group which may have a substituent, $X^1$ is a halogen atom, m1, n1 are each 0 or 1, and m1+n1 is 1 or 2);

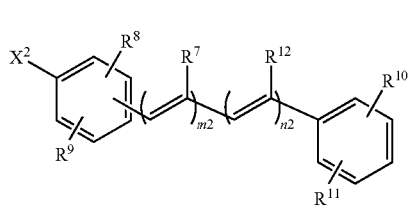

(4b)

(In the general formula (4b), $R^7$ to $R^{12}$ each are a hydrogen atom, an alkyl group which may have a substituent, an alkoxy group which may have a substituent, a phenoxy group which may have a substituent, an aryl group which may have a substituent, or an aralkyl group which may have a substituent, $X^2$ is a halogen atom, m2, n2 are each 0 or 1, and m2+n2 is 1 or 2); and

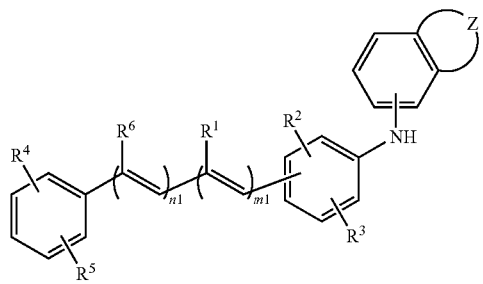

(5)

(In the general formula (5), $R^1$ to $R^6$ each are a hydrogen atom, an alkyl group which may have a substituent, an alkoxy group which may have a substituent, a phenoxy group which may have a substituent, an aryl group which may have a substituent, or an aralkyl group which may have a substituent, Z is a ring structure linked to a benzene ring, which is a 4 to 8-membered ring including a hydrogen atom, a nitrogen atom, an oxygen atom, a carbon atom or a sulfur atom, m1, n1 are each 0 or 1, and m1+n1 is 1 or 2.)

5. The production method for a diphenyl amine derivative according to claim 4, wherein a palladium compound is used as a catalyst in steps (A) and (B), or in either of steps.

6. The production method for a diphenyl amine derivative according to claim 4, wherein steps (A) and (B), or either of the steps are carried out in the presence of a base.

7. An electrophotographic photoconductor comprising a photoconductor layer provided on a conductive base member, wherein the photoconductor layer contains the diphenyl amine derivative according to claim 1.

8. The electrophotographic photoconductor according to claim 7, wherein the photoconductor layer is a monolayer type photoconductor layer and the content of the diphenyl amine derivative is a value in a range of 20 to 500 parts by weight with respect to 100 parts by weight of the binding resin of the photoconductor layer.

9. The electrophotographic photoconductor according to claim 7, wherein the photoconductor layer is a multilayer type photoconductor layer and the content of the diphenyl amine derivative is a value in a range of 10 to 500 parts by weight with respect to 100 parts by weight of the binding resin of the charge transfer layer included in the photoconductor layer.

* * * * *